US012779175B2

(12) United States Patent
Thissen

(10) Patent No.: US 12,779,175 B2
(45) Date of Patent: Nov. 3, 2026

(54) METHOD OF MANUFACTURING A TUBE WITH A PLAYLESS HINGE AND DEVICE COMPRISING SUCH A TUBE

(71) Applicant: Fortimedix Assets II B.V., Geleen (NL)

(72) Inventor: Mattheus Hendrik Louis Thissen, Swalmen (NL)

(73) Assignee: Fortimedix Assets II B.V., Geleen (NL)

( * ) Notice: Subject to any disclaimer, the term of this patent is extended or adjusted under 35 U.S.C. 154(b) by 0 days.

(21) Appl. No.: 19/253,560

(22) Filed: Jun. 27, 2025

(65) Prior Publication Data

US 2026/0002617 A1 Jan. 1, 2026

Related U.S. Application Data

(60) Provisional application No. 63/666,266, filed on Jul. 1, 2024.

(51) Int. Cl.

| | |
|---|---|
| ***A61M 25/01*** | (2006.01) |
| ***B23K 26/38*** | (2014.01) |
| ***F16L 27/08*** | (2006.01) |
| *A61B 17/00* | (2006.01) |
| *B23K 101/06* | (2006.01) |

(52) U.S. Cl.
CPC ......... *A61M 25/0138* (2013.01); *B23K 26/38* (2013.01); *F16L 27/0861* (2013.01); *A61B 2017/00309* (2013.01); *B23K 2101/06* (2018.08)

(58) Field of Classification Search
CPC ....... F16L 27/0861; A61B 2017/00314; A61B 1/0055; A61B 2017/00309
USPC ......................................... 285/148.1, 148.13
See application file for complete search history.

(56) References Cited

U.S. PATENT DOCUMENTS

| | | | |
|---|---|---|---|
| 2,515,366 A | | 7/1950 | Zublin |
| 2,717,146 A | | 9/1955 | Zublin |
| 3,788,304 A | | 1/1974 | Takahashi |
| 4,362,520 A | | 12/1982 | Perry |
| 4,706,659 A | | 11/1987 | Matthews et al. |
| 4,745,908 A | | 5/1988 | Wardle |
| 5,271,381 A | | 12/1993 | Ailinger et al. |
| 5,749,828 A | | 5/1998 | Solomon et al. |
| 5,807,241 A | | 9/1998 | Heimberger |
| 5,857,964 A | * | 1/1999 | Konstorum .......... A61B 1/0055 600/141 |
| 5,928,136 A | | 7/1999 | Barry |

(Continued)

FOREIGN PATENT DOCUMENTS

| | | |
|---|---|---|
| CH | 81017 A | 5/1919 |
| CN | 101522121 B | 9/2011 |

(Continued)

OTHER PUBLICATIONS

International Search Report and Written Opinion mailed Sep. 26, 2025, International Application No. PCT/EP2025/068611, 14 pages.

*Primary Examiner* — David Bochna
(74) *Attorney, Agent, or Firm* — Fortem IP LLP

(57) ABSTRACT

Disclosed herein are examples of playless hinge designs formed in a tubular member and methods of making playless hinge designs. The playless hinge designs may, for example, be formed in a tubular member in an articulable tube assembly (e.g., medical instrument), and may exhibit reduced axial and/or tangential play when being articulated.

20 Claims, 15 Drawing Sheets

(56) References Cited

U.S. PATENT DOCUMENTS 6,107,004 A 8/2000 Donadio, III
6,450,948 B1 9/2002 Matsuura et al.
6,890,329 B2 5/2005 Carroll et al.
7,189,228 B2 3/2007 Eum et al.
7,320,700 B2 1/2008 Cooper et al.
7,553,275 B2 6/2009 Padget et al.
7,615,067 B2 11/2009 Lee et al.
8,257,267 B2 9/2012 Thornton
8,323,241 B2 12/2012 Salahieh et al.
8,327,518 B2 12/2012 Eberhard
8,382,742 B2 2/2013 Hermann et al.
8,398,587 B2 3/2013 Dewaele et al.
8,708,954 B2 4/2014 Webler
8,740,884 B2 6/2014 Verbeek
8,845,522 B2 9/2014 McIntyre et al.
8,882,680 B2 11/2014 Furlong et al.
8,986,317 B2 3/2015 Verbeek
9,072,505 B2 7/2015 Furlong et al.
9,138,566 B2 9/2015 Cabiri
9,198,561 B2 12/2015 Smith et al.
9,220,398 B2 12/2015 Woodley et al.
9,339,271 B2 5/2016 Ranucci et al.
9,421,343 B2 8/2016 Berthiaume et al.
9,462,932 B2 10/2016 Ostrovsky et al.
9,468,359 B2 10/2016 Weisshaupt et al.
9,655,637 B2 5/2017 Mueller
9,848,858 B2 12/2017 Verbeek
9,877,720 B2 1/2018 Worrell et al.
10,010,246 B2 7/2018 Quaye
10,265,087 B2 4/2019 Furlong et al.
10,405,876 B2 9/2019 Boudreaux
10,420,537 B2 9/2019 Salahieh et al.
10,441,746 B2 10/2019 Besselink
10,449,010 B2 10/2019 Dewaele et al.
10,456,556 B2 10/2019 Cabiri
10,485,579 B2 11/2019 Lenker
10,492,771 B2 12/2019 Nunan
10,500,373 B2 12/2019 Barrish et al.
10,524,868 B2 1/2020 Cooper et al.
10,542,878 B2 1/2020 Dewaele et al.
10,561,467 B2 2/2020 Van Der Linde et al.
10,603,047 B2 3/2020 Ding et al.
10,646,104 B1 5/2020 Sinay et al.
10,729,457 B2 8/2020 Lenker et al.
10,792,061 B2 10/2020 Dewaele et al.
10,799,223 B2 10/2020 Furlong et al.
10,874,290 B2 12/2020 Walen et al.
10,962,093 B2 3/2021 Dewaele et al.
11,007,026 B2 5/2021 Kowshik
11,033,255 B2 6/2021 Furlong et al.
11,051,794 B2 7/2021 Cooper et al.
11,052,226 B2 7/2021 Salahieh et al.
11,103,234 B2 8/2021 Felix et al.
11,130,244 B2 9/2021 Jogasaki
11,134,928 B2 10/2021 Felix et al.
11,141,566 B2 10/2021 Cabiri
11,241,557 B2 2/2022 Besselink
11,278,704 B2 3/2022 Pleijers
11,330,964 B2 5/2022 Thissen
11,350,914 B2 6/2022 Furlong et al.
11,382,654 B2 7/2022 Lenker
11,419,691 B2 8/2022 Kim et al.
11,457,904 B2 10/2022 Dewaele et al.
11,523,807 B2 12/2022 Furlong et al.
11,564,670 B2 1/2023 Furlong et al.
11,576,735 B2 2/2023 Blanckaert et al.
11,589,733 B2 2/2023 Sinay et al.
11,607,242 B2 3/2023 Tada et al.
11,642,114 B2 5/2023 Thissen
11,660,101 B2 5/2023 Walen et al.
11,696,677 B2 7/2023 Thissen
11,730,921 B2 8/2023 Besselink
11,730,927 B2 8/2023 Laby et al.
11,839,401 B2 12/2023 Lenker
12,048,819 B2 7/2024 Yang et al.
12,295,550 B2 5/2025 Tilson et al.
2004/0199052 A1 10/2004 Banik et al.
2004/0236316 A1 11/2004 Danitz et al.
2005/0027245 A1 2/2005 Sachdeva et al.
2005/0273084 A1 12/2005 Hinman et al.
2005/0273085 A1 12/2005 Hinman et al.
2006/0199999 A1 9/2006 Ikeda et al.
2006/0281566 A1 12/2006 Lee
2007/0049800 A1 3/2007 Boulais
2007/0250113 A1 10/2007 Hegeman et al.
2007/0282371 A1 12/2007 Lee et al.
2007/0287993 A1 12/2007 Hinman et al.
2008/0249364 A1 10/2008 Korner
2008/0300462 A1 12/2008 Intoccia et al.
2009/0069632 A1 3/2009 McIntyre et al.
2009/0124857 A1 5/2009 Viola
2010/0151161 A1 6/2010 Da Rolo
2010/0228191 A1 9/2010 Alvarez et al.
2010/0234831 A1 9/2010 Hinman et al.
2010/0286480 A1 11/2010 Peine et al.
2010/0287755 A1 11/2010 Eberhard
2011/0004157 A1 1/2011 Dewaele et al.
2011/0295065 A1 12/2011 Gurusamy et al.
2012/0116163 A1 5/2012 Lutze et al.
2012/0245414 A1 9/2012 Verbeek
2012/0277730 A1 11/2012 Salahieh et al.
2012/0323077 A1 12/2012 Verbeek
2013/0184528 A1 7/2013 Onuki et al.
2013/0197490 A1 8/2013 Stanton et al.
2013/0253469 A1 9/2013 Freed
2014/0018620 A1 1/2014 Verbeek
2014/0249474 A1 9/2014 Suon et al.
2015/0099997 A1 4/2015 Cabiri
2015/0107396 A1 4/2015 Suehara
2015/0112134 A1 4/2015 Suehara et al.
2015/0157353 A1 6/2015 Lenker et al.
2015/0352728 A1 12/2015 Wang
2015/0366445 A1 12/2015 Rutgers
2016/0015249 A1 1/2016 Suehara
2016/0096004 A1 4/2016 Gerrans et al.
2016/0136393 A1 5/2016 Tsai et al.
2016/0278616 A1 9/2016 Viebach et al.
2017/0027607 A1 2/2017 Verbeek et al.
2018/0049873 A1 2/2018 Manash et al.
2018/0055589 A1 3/2018 Joseph et al.
2018/0056040 A1* 3/2018 Fenech ............. A61M 25/0138
2018/0289241 A1 10/2018 Zhou et al.
2019/0111237 A1 4/2019 Cabiri
2019/0111238 A1 4/2019 Schultz et al.
2019/0175869 A1 6/2019 Kirt et al.
2020/0205908 A1 7/2020 Julian et al.
2020/0275983 A1 9/2020 Dewaele et al.
2020/0330729 A1 10/2020 Petitpierre et al.
2021/0267702 A1 9/2021 Kim et al.
2021/0275266 A1 9/2021 Kim et al.
2021/0316115 A1* 10/2021 Yang .................... A61B 1/0011
2021/0378648 A1 12/2021 Thissen et al.
2022/0061634 A1 3/2022 Thissen et al.
2022/0087666 A1 3/2022 Sharma et al.
2022/0117576 A1 4/2022 Mixter et al.
2022/0167836 A1 6/2022 Thissen et al.
2022/0168008 A1 6/2022 Thissen et al.
2022/0331003 A1 10/2022 Cohen et al.
2023/0031313 A1 2/2023 Lynn et al.
2023/0131647 A1 4/2023 Magno et al.
2023/0165573 A1 6/2023 Furlong et al.
2023/0190329 A1 6/2023 Tada et al.
2023/0255644 A1 8/2023 Walen et al.
2023/0355385 A1* 11/2023 Shally ............... A61M 25/0138
2024/0138946 A1 5/2024 Swoyer et al.
2024/0173130 A1 5/2024 McNiven et al.
2024/0206715 A1 6/2024 Kunuki et al.
2024/0216008 A1 7/2024 Lenker
2024/0245284 A1 7/2024 Thissen
2024/0252026 A1 8/2024 Hornak et al.
2024/0306900 A1 9/2024 Thissen et al.
2024/0389835 A1 11/2024 Thissen et al.
2025/0049305 A1 2/2025 Thissen

(56) References Cited

U.S. PATENT DOCUMENTS

| | | | | |
|---|---|---|---|---|
| 2025/0049307 | A1 | 2/2025 | Thissen | |
| 2025/0204755 | A1* | 6/2025 | Lander ............... | A61B 1/00149 |
| 2025/0204758 | A1* | 6/2025 | Lander ............. | A61B 17/00234 |

FOREIGN PATENT DOCUMENTS

| | | | |
|---|---|---|---|
| CN | 118662079 | A | 9/2024 |
| DE | 3219629 | A1 | 12/1983 |
| DE | 4222121 | C1 | 9/1993 |
| DE | 102009037030 | A1 | 2/2011 |
| DE | 102010005243 | A1 | 7/2011 |
| DE | 102010000787 | B4 | 9/2014 |
| EP | 0626604 | A2 | 11/1994 |
| JP | 2012075659 | A | 4/2012 |
| JP | 2015213758 | A | 12/2015 |
| KR | 101312071 | B1 | 9/2013 |
| NL | 2030160 | B1 | 6/2023 |
| WO | 1997042910 | A1 | 11/1997 |
| WO | 2004103430 | A2 | 12/2004 |
| WO | 2008139768 | A1 | 11/2008 |
| WO | 2010105649 | A1 | 9/2010 |
| WO | 2011018147 | A1 | 2/2011 |
| WO | 2011018179 | A2 | 2/2011 |
| WO | 2011079897 | A1 | 7/2011 |
| WO | 2012035531 | A1 | 3/2012 |
| WO | 2013084985 | A1 | 6/2013 |
| WO | 2014186736 | A1 | 11/2014 |
| WO | 2015085307 | A1 | 6/2015 |
| WO | 2016054063 | A1 | 4/2016 |
| WO | 2017010883 | A2 | 1/2017 |
| WO | 2017014624 | A1 | 1/2017 |
| WO | 2017082720 | A1 | 5/2017 |
| WO | 2023287286 | A2 | 1/2023 |
| WO | 2024033706 | A1 | 2/2024 |
| WO | 2025026670 | A1 | 2/2025 |
| WO | 2025026702 | A1 | 2/2025 |

* cited by examiner (PRIOR ART)

METHOD OF MANUFACTURING A TUBE WITH A PLAYLESS HINGE AND DEVICE COMPRISING SUCH A TUBE

CROSS-REFERENCE TO RELATED APPLICATION(S)

The present application claims the benefit of priority to U.S. Provisional Patent Application No. 63/666,266, filed Jul. 1, 2024, which is incorporated by reference herein in its entirety.

TECHNICAL FIELD

The present technology relates to the design of playless hinge structures in an articulable tube.

BACKGROUND

Steerable catheters are widely used in minimally invasive medical procedures to navigate through tortuous anatomical pathways and reach target locations within the human body. Conventional steerable catheters typically employ steering wires or pull wires that extend along the length of the catheter shaft and are mechanically coupled to the distal tip. When tension is applied to these steering wires through a proximal control mechanism, the distal end of the catheter deflects in a predetermined direction to facilitate navigation through complex vascular or anatomical structures.

However, steering wire-based catheter systems present several technical challenges that can limit their effectiveness and precision during medical procedures. For example, the mechanical coupling between the steering wires and the catheter tip may result in unpredictable deflection characteristics. Additionally, the transmission of force from the proximal control mechanism to the distal tip through the steering wires can be inconsistent due to wire material properties and friction losses along the catheter shaft. These factors can lead to reduced responsiveness, reduced lifetime use of the catheter system, imprecise tip positioning, and difficulty maintaining desired catheter orientations during complex navigational maneuvers, thereby potentially compromising procedural outcomes and requiring additional time and effort from medical practitioners.

Accordingly, there is a need for improved steering and other articulable devices for medical procedures.

BRIEF DESCRIPTION OF THE DRAWINGS

Further features and advantages of the present technology will become apparent from the description of the present technology by way of non-limiting and non-exclusive embodiments. These embodiments are not to be construed as limiting the scope of protection. The person skilled in the art will realize that other alternatives and equivalent embodiments of the present technology can be conceived and reduced to practice without departing from the scope of the present technology.

Many aspects of the present disclosure can be better understood with reference to the following drawings. The components in the drawings are not necessarily to scale. Instead, emphasis is placed on illustrating clearly the principles of the present disclosure.

Figure 1:
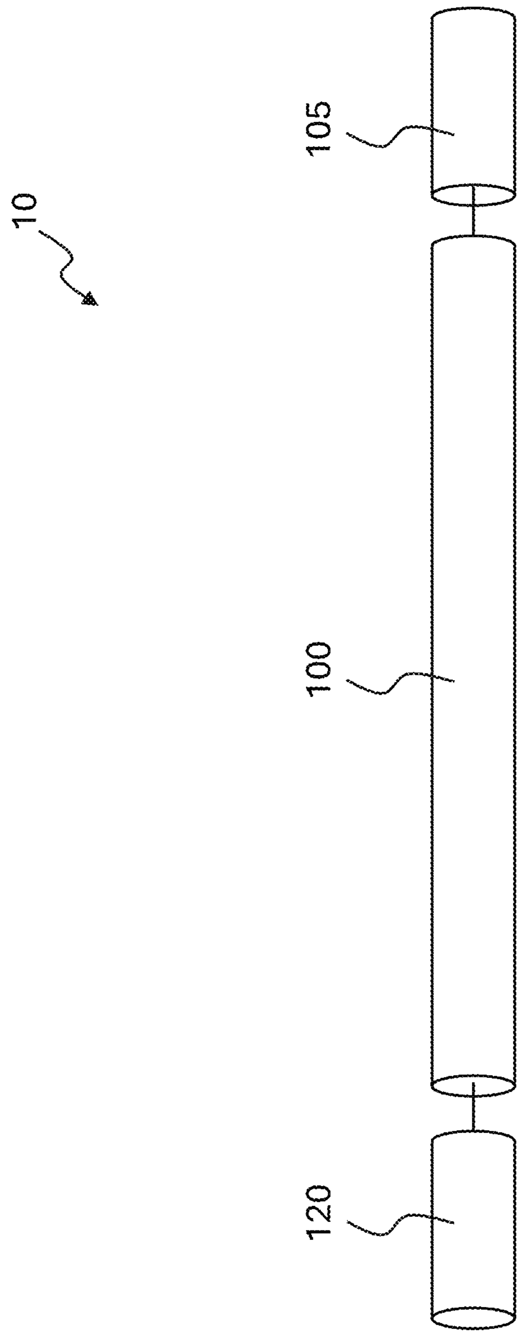
FIG. 1 depicts an example steerable device, in accordance with the present technology.

For the purpose of the present document, the terms cylindrical element and tube may be used interchangeably, i.e., like the term tube a cylindrical element also refers to a physical entity. The cross section of such tubes may be circular in most applications but that need not be the case. For instance, they may be oval, or rectangular. The present technology will be explained with reference to tendons which are cut from such cylindrical elements and are operative to transfer longitudinal movement of the tendons at, for example, the proximal end of the instrument to the distal end to thereby control bending of one or more flexible distal end portions. Embodiments in which reduction of play in hinges is explained can also be implemented with wires made in a classic way and not resulting from cutting them out of a tube. Moreover, tendons can, alternatively or additionally, be used for functions other than controlling bending of one or more flexible distal portions, such as lock/unlock or increasing friction between elements of the instrument, as explained, for example in PCT International Publication No. WO2023/287289, which is incorporated herein in its entirety by this reference.

DETAILED DESCRIPTION

The present technology relates to a playless hinge structure for a steerable tube, such as for a steerable tube assembly. Some embodiments of the present technology, for example, are directed to hinges in a steerable tube assembly for a medical instrument such as for endoscopic or catheter applications. Specific details of several embodiments of the technology are described below with reference to FIGS. 1-22B.

As used herein, the terms "proximal" and "distal" are defined with respect to an operator, e.g., a robot or physician that operates the instrument, catheter, or endoscope. For example, a proximal end part is to be construed as a part that is located near the robot or physician and a distal end part as a part located at a distance from the robot or physician, such as in the area of operation.

The present technology relates to a tube for an articulable instrument such as a medical instrument (e.g., for endoscopic and/or invasive type of applications, such as in surgery) or other articulable devices. The articulable instrument can be used in both medical and non-medical applications. Examples of the latter include inspection and/or repair of mechanical and/or electronic hardware at locations that are difficult to reach (e.g., optical devices, plumbing devices, etc.). Hence, terms used in the following description such as endoscopic application or invasive instrument, must be interpreted in a broad manner.

I. Articulable Tube Assembly

In some embodiments, an articulable device may include an articulable tube assembly having one or more articulable regions along its length, where the one or more articulable regions are configured to articulate (e.g., bend, curve, etc.). In some embodiments, an articulable region may be configured to articulate passively (e.g., in response to articulating movement of a stylet or an outer sheath telescopically engaged with the articulable region). For example, an articulable region may include a wrist region of an instrument (e.g., for manual, robotic, or robotic-assisted laparoscopy). Additionally or alternatively, in some embodiments, an articulable region may be configured to articulate in response to one or more steering inputs. For example, in some embodiments, the articulable tube assembly may be configured to receive one or more steering inputs at a first location along the length of the articulable tube assembly, and the articulable tube assembly may be configured to communicate and/or transform the steering input(s) into articulation at one or more articulable regions located at at least a second location along the length of the articulable tube assembly, where the second location is distal to the first location. For example, in some embodiments, the one or more steering inputs may be located at a proximal portion of the articulable tube assembly, and the articulable region(s) may be located at an intermediate portion and/or distal portion of the articulable tube assembly. In some embodiments, the articulable tube assembly may include multiple elongated members (e.g., tubular members) that are arranged coaxially, such as in a nested manner. The multiple elongated members may have respective articulable regions that are longitudinally aligned, such that when the multiple elongate members are assembled together in an articulable tube assembly, their articulable regions are configured to be shaped and articulate in tandem. In some embodiments, an actuating input may be applied to a portion (e.g., proximal portion, intermediate portion, or other portion that is longitudinally distanced from an articulable region) of one elongate member (e.g., an outer elongate member), and that actuating input may be communicated to a steering feature such as a tendon (as described in further detail below) on an underlying elongate member to cause collective articulation of the multiple assembled elongate members. Further details of example articulable devices and articulable tube assemblies are described below. Although examples of an articulable tube assembly are primarily described herein as a steerable tube assembly, it should be understood that at least some aspects of an articulable tube assembly may be similarly incorporated in a tube assembly that is passively articulated (e.g., in response to articulating movement of a stylet arranged within the tube assembly, movement of an outer tube arranged outside the tube assembly, and/or the like).

FIG. 1 is a schematic illustration of an example articulable device 10 (also referred to herein as a steerable device) including a steerable tube assembly 100. As shown schematically in FIG. 1, the steerable device 10 may be coupled to at least one actuator 105 configured to provide a steering input to the steerable device 10. In some embodiments, the steerable device may be coupled to the at least one actuator 105 at an end portion (e.g., proximal end portion, distal end portion) and/or at an interior portion of the steerable device. Although FIG. 1 illustrates schematically an actuator 105 that is coupled end-to-end with the steerable tube assembly 100, it should be understood that this arrangement is representative, and the actuator 105 may be coupled to the steerable tube assembly 100 in any suitable manner. For example, the actuator 105 may be coupled to an end portion of the steerable tube assembly 100 so as to provide an actuating input directed radially inward toward the end portion of the steerable tube assembly. The actuating input may include an input in a longitudinal (e.g., translational) direction and/or circumferential (e.g., rotational) direction, for example. In some embodiments, the actuating input may be manual (e.g., controlled by a human operator) and/or robotic.

As shown schematically in FIG. 1, the steerable device 10 may be coupled at an end portion (e.g., a distal end portion) to at least one end effector 120. The end effector 120 may include a tool (e.g., graspers, scissors, ablation tool, etc.), a sensor (e.g., camera, electrode, etc.) and/or any suitable instrument. Components useful for operation of the end effector 120, such as wires for actuation of a tool, signal transmission, and/or electrical power transmission, may be passed along one or more lumens defined within the steerable tube assembly 100. In some embodiments, no end effector 120 is coupled to the steerable device 10; for example, the steerable device 10 may be a catheter (e.g., delivery catheter).

Figure 2A:
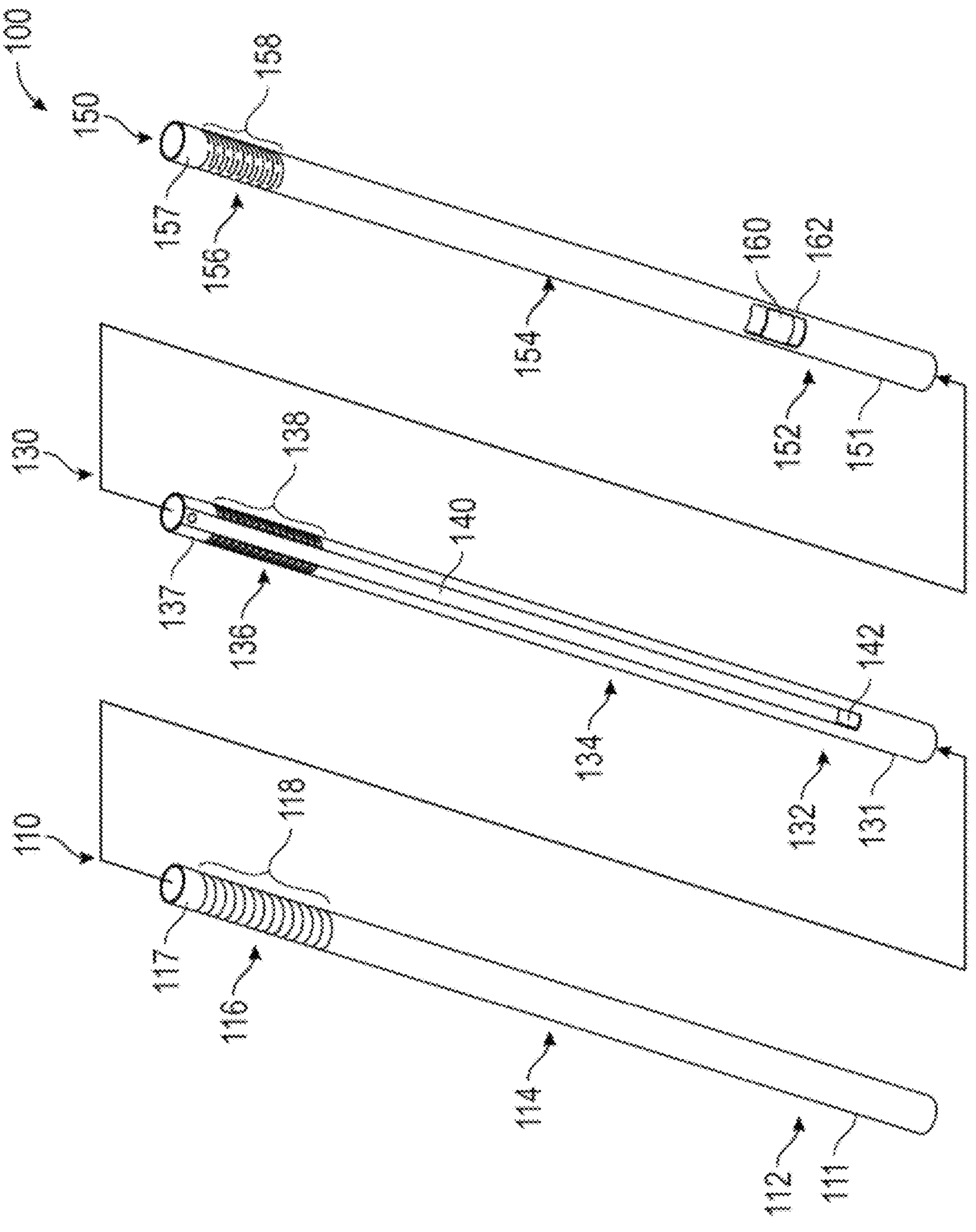
FIG. 2A depicts an exploded view of an example steerable tube assembly, in accordance with the present technology.

As described above, in some embodiments, a steerable tube assembly may include multiple, coaxial elongate tubular members. For example, as shown in FIG. 2A, an example steerable tube assembly may include an inner member 110, an outer member 150, and an intermediate member 130 arranged between the inner member 110 and the outer member 150. The inner member 110 may be inserted into a lumen of the intermediate member 130, and the intermediate member 130 may be inserted into a lumen of the outer member 150. Although FIG. 2A illustrates an example in which the steerable tube assembly includes a single intermediate member 130, it should be understood that in some embodiments, the steerable tube assembly may include two, three, or more intermediate members arranged between the inner member 110 and the outer member 150, where each intermediate member may have a respective set of operable features. As such, a steerable tube assembly may include any suitable number of nested, coaxial tubular members (e.g., two, three, four, or more than four); however, for sake of simplicity of explanation, a representative steerable tube assembly 100 with three elongate members is primarily described herein. In some embodiments, an articulable device may include only a single tubular member incorporating at least some features of elongate members as described herein.

The inner member 110 may include a proximal portion 112 including a proximal end 111, a distal portion 116 including a distal end 117, and an intermediate portion 114 arranged between the proximal and distal ends of the inner member 110. The inner member 110 may further include at least one articulable region 118 configured to articulate (e.g., bend, curve, etc.). In some embodiments, the proximal end 111 and/or distal end 117 may be non-articulable (e.g., rigid). Although FIG. 2A illustrates an example in which the inner member 110 includes one articulable region 118 located generally in the distal portion 116, it should be understood that in some embodiments, the inner member 110 may include two or more (e.g., two, three, four, more than four, etc.) articulable regions 118 arranged at any suitable location(s) along the length of the inner member 110, including in the proximal portion 112, intermediate portion 114, and the distal portion 116.

The articulable region 118 may include one or more articulating features configured to enable the articulable region 118 to assume a suitable articulated shape (e.g., bent, curved, etc.). For example, as shown in FIG. 2A, the articulable region 118 may include a plurality of circumferential (or helical, etc.) slots. As described in further detail herein, the slots may, for example, be formed by cutting any suitable pattern from the wall of the inner member 110. In some embodiments, dimensional aspects of the hinge pattern in the articulable region 118 (e.g., longitudinal length of the articulable region 118, size and shape of slots forming hinges, hinge spacing, etc.) may be selected or otherwise predetermined to accommodate specific performance requirements, such as with regard to bending angle, bending flexibility, longitudinal stiffness, and/or radial stiffness of the articulable region 118.

Similar to the inner member, the outer member 150 may include a proximal portion 152 including a proximal end 151, a distal portion 156 including a distal end 157, and an intermediate portion 154 arranged between the proximal and distal ends of the outer member 150. The outer member 110 may further include at least one articulable region 158 configured to articulate (e.g., bend, curve, etc.). In some embodiments, the proximal end 151 and/or distal end 157 may be non-articulable (e.g., rigid). Although FIG. 2A illustrates an example in which the outer member 150 includes one articulable region 158 located generally in the distal portion 156, it should be understood that in some embodiments, the outer member 150 may include two or more (e.g., two, three, four, more than four, etc.) articulable regions 158 arranged at any suitable location(s) along the length of the outer member 150, including in the proximal portion 152, intermediate portion 154, and the distal portion 156. The one or more articulable regions 158 may be constructed in a similar manner to the articulable region(s) 118 of the inner member 110, though the articulable region (s) 158 may have a different specific hinge pattern than the articulable region(s) 118.

The intermediate member 130 may include a proximal portion 132 including a proximal end 131, a distal portion 136 including a distal end 137, and an intermediate portion 134 arranged between the proximal and distal ends of the intermediate member 130. The intermediate member 130 may further include at least one articulable region 138 configured to articulate (e.g., bend, curve, etc.), although in some embodiments the intermediate member 130 may lack or omit articulable region(s) 138. In some embodiments, the proximal end 131 and/or distal end 137 may be non-articulable (e.g., rigid). Although FIG. 2A illustrates an example in which the intermediate member 130 includes one articulable region 138 located generally in the distal portion 136, it should be understood that in some embodiments, the intermediate member 130 may include two or more (e.g., two, three, four, more than four, etc.) articulable regions 138 arranged at any suitable location(s) along the length of the intermediate member 130, including in the proximal portion 132, intermediate portion 134, and the distal portion 136. The one or more articulable regions 138 may be constructed in a similar manner to the articulable region(s) 118 of the inner member 110, though the articulable region(s) 138 may have a different specific hinge pattern than the articulable region(s) 118 of the inner member 110 and/or the articulable region(s) 158 of the outer member 150.

Figure 2B:
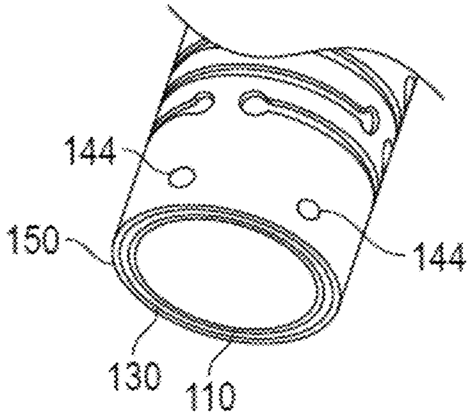
FIG. 2B depicts a detailed view of a portion of an example steerable tube assembly, in accordance with the present technology.

The inner member 110, the intermediate member 130, and the outer member 150 may be assembled to form a combined unit within the steerable tubular assembly. For example, the inner member 110 may be inserted into the intermediate member 130, and the combined inner member 110 and intermediate member 130 subassembly may be inserted into the outer member 150, although any order of insertion may be possible. In some embodiments, only two elongate members (e.g., the inner member 110 and the intermediate member 130, the inner member 110 and the outer member 150, or the intermediate member 130 and the outer member 150) may be assembled to form a combined unit within the steerable tubular assembly. In some embodiments, the proximal ends 111, 131, 151 of the inner member 110, the intermediate member 130, and/or the outer member 150, respectively, may be coupled to one another so as to be fixed together. Similarly, the distal ends 117, 137, 157 of the inner member 110, the intermediate member 130, and/or the outer member 150, respectively, may additionally or alternatively be coupled to one another so as to be fixed together. Such coupling of the proximal ends 111, 131, 151 and/or coupling of the distal ends 117, 137, 157 may accomplished in any suitable manner, such as with epoxy, welding (e.g., laser welding), or mechanical interfit (e.g., press fit). For example, FIG. 2B provides a more detailed view of a distal end portion of an example steerable tube assembly including three co-axially arranged layers or tubular members, including inner member 110, intermediate member 130, and outer member 150. The distal ends of the inner member 110, the intermediate member 130, and the outer member 150 may be fixedly attached to one another, such as with one or more spot welds 144. In some embodiments, multiple spot welds 144 may be arranged circumferentially around the steerable tube assembly, either equally distributed or unequally distributed around the circumference of the steerable tube assembly. The spot welds 144 may be arranged at the proximal ends 111, 131, and/or 151, and/or at the distal ends 117, 137, and/or 157, and/or at any suitable axial location along the length of the steerable tubular assembly.

As shown in FIG. 2A, the intermediate member 130 may further include one or more tendons 140 each coupled to (e.g., integrally formed with, attached to) and/or extending through a respective articulable region 138, such that movement of a tendon 140 causes articulation of its corresponding articulable region 138 in a bending direction. In some embodiments, a distal end of a tendon 140 may be coupled to (e.g., integrally formed with, or attached such as via at least one weld) to the distal end 137 of the intermediate member 130.

Figure 5:
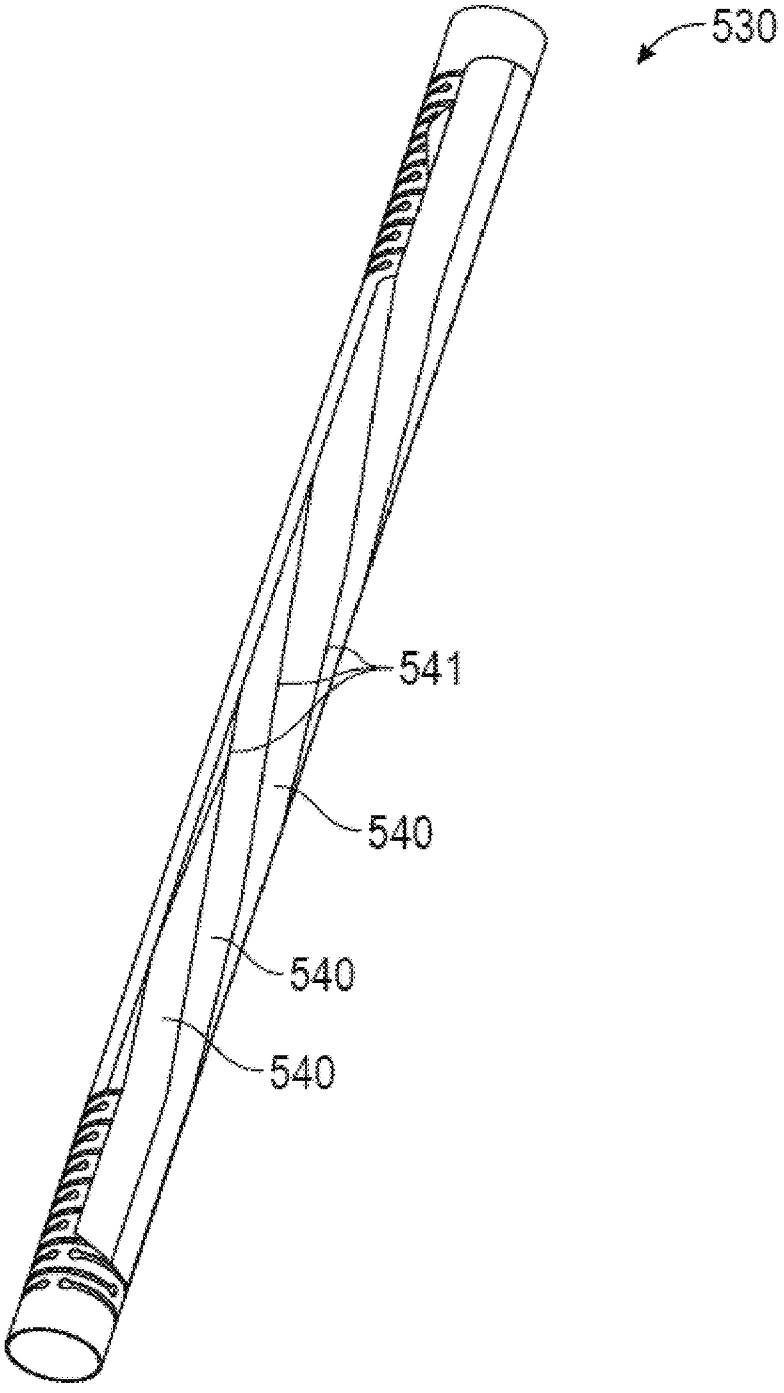
FIG. 5 shows an example intermediate member and an inner member inserted in the intermediate member, in accordance with the present technology.

A tendon 140 may be formed as a longitudinal member or strip extending longitudinally along at least a portion of a wall of the intermediate member 130, for at least a portion of the length of the intermediate member 130. A tendon 140 may be configured to move generally in a longitudinal direction within a respective slot 142. In the example shown in FIG. 2A, the slot 142 is generally linear and extends in a longitudinal direction. However, in some embodiments the slot 142 may be any suitable shape generally extending in a longitudinal direction, such as a helical shape that wraps in a spiral manner around the wall of the intermediate member 130. A tendon 140 may have any suitable corresponding shape to travel within the slot 142 (e.g., a helical tendon 140 configured to travel generally in a proximal and/or distal direction within a helical slot 142). For example, FIG. 5 illustrates an example intermediate member 430 (an example of intermediate member 130) that includes multiple helical tendons 540 that have been obtained after forming longitudinal cuts 541 in the wall of the intermediate member 530. As shown in FIG. 5, the tendons 540 are, at least in part, spiraling about a longitudinal axis of the intermediate member 530 such that a proximal portion of a given tendon 540 is arranged at a different angular orientation about the longitudinal axis than a distal portion of the same given tendon 540. In some embodiments, the spiral construction may be such that the proximal end portion of a tendon 540 is arranged at an angularly shifted orientation of 180 degrees about the longitudinal axis relative to the distal end portion of the same tendon 540. However, the angularly shifted orientation between the two end portions of a tendon 540 may be any suitable angle (e.g., 45 degrees, 60 degrees, 75 degrees, 90 degrees, etc.). The cuts 541 may form a slot (e.g., similar to slot 142) therebetween, and may be dimensioned such that movement of a tendon 540 is guided at least in part by adjacent tendons 540 when provided in a steerable device.

In some embodiments, a tendon 140 may be actuated via an actuating input applied to a feature of the outer member 150. For example, as shown in FIG. 2A, in some embodiments, the outer member 150 may include at least one slider 160 configured to move within a respective slot 162. Each slider 160 may be coupled to an underlying tendon 140 (e.g., via epoxy, spot welding, etc.) such that movement of the slider 160 results in movement of its associated tendon 140. The outer member 150 may include multiple sliders 160, where each slider 160 is coupled to a respective tendon 140, such as selective actuation of the sliders 160 results in selective movement of tendons 140 and thus selective articulation of articulable regions of the members of the steerable tube assembly. Although the slot 162 is shown in FIG. 2A as generally linear such that the slider 160 moves longitudinally along the outer tube 150 (e.g., to push and/or pull a tendon 140 to which the slider 160 is coupled), it should be understood that in some embodiments, the slider 160 may move at least partially in a rotational manner in an arcuate slot 162 (e.g., the slider 160 may be configured to move in a helical manner along a helical slot 162, which may, for example, thereby cause movement of an underlying tendon 140 to which the slider 160 is connected.

Furthermore, although only one tendon 140 is visible in the example shown in FIG. 2A, the intermediate member 130 may include any suitable number of tendons 140. For example, in some embodiments a second tendon 140 may be located on a circumferentially opposite side of the intermediate member 130. For example, two tendons 140 may be circumferentially offset about 180 degrees from one another and operate in an antagonistic manner to articulate an articulable region 138 to which the two tendons 140 are coupled. For instance, a first tendon 140 may be pulled proximally in a longitudinal direction (and/or a second tendon 140 arranged circumferentially opposite to the first tendon 140 may be pushed distally in a longitudinal direction) to cause bending of the articulable region 138 in a first direction. The second tendon 140 may be pulled proximally in a longitudinal direction (and/or the first tendon 140 may be pushed distally in a longitudinal direction) to cause bending of the articulable region 138 in a second direction (e.g., opposite the first direction).

In some embodiments, the intermediate member 130 may include more than one, or more than two tendons 140. For example, the intermediate member 130 may include three or more tendons 140 coupled to a common articulable region 138. In some embodiments, multiple tendons 140 may be circumferentially spaced apart in an equidistant manner (e.g., the tendons may be located at equidistant locations as viewed in the tangential direction of the intermediate member 130), though in some embodiments an intermediate member 130 may additionally or alternatively include multiple tendons 140 that are circumferentially spaced apart in an unequal manner.

Additionally or alternatively, the intermediate member 130 may include one or more tendons 140 each coupled to a different articulable region 138. For example, a first pair of antagonistic tendons 140 may be coupled to a first articulable region 138 (e.g., arranged at a first axial location along the length of the intermediate member 130), and a second pair of antagonistic tendons 140 may be coupled to a second articulable region 138 (e.g., arranged, at a second axial location along the length of the intermediate member 130). In some embodiments, the intermediate member 130 may include multiple tendons 140 of substantially equal length, though in some embodiments the intermediate member 130 may additionally or alternatively include multiple tendons 140 of different lengths.

In some embodiments, articulable region(s) of the inner member 110, the intermediate member 130, and/or the outer member 150 may be longitudinally aligned with or at least overlap with one another when the inner, intermediate, and outer members are assembled together in the steerable tube assembly. As such, when articulable region(s) 138 are articulated (via actuation of one or more tendons 140), the underlying articulable region(s) 118 of the inner member and the overlying articulable region(s) 158 of the outer member are passively articulated to follow or generally match the shape of the articulable region(s) 138 of the intermediate member.

Figure 3:
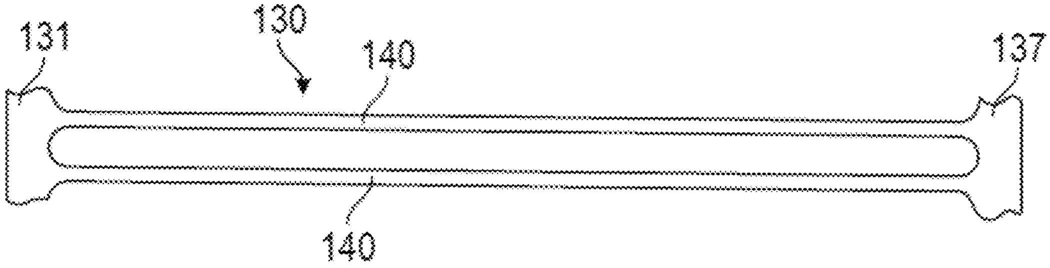
FIG. 3 depicts an unwrapped view of an example tube with tendons in an example steerable tube assembly, in accordance with the present technology.

In some embodiments, the intermediate member 130 may include one or more tendons 140 having a substantially uniform cross-section (e.g., width) along its length. For example, FIG. 3 illustrates an example of an intermediate member 130 in an unrolled condition including two parallel tendons 140 having substantially uniform cross-section along their length between the proximal end 131 of the intermediate member and the distal end 137 of the intermediate member. In the example shown in FIG. 3, the tendons 140 are attached at both the proximal end 131 and the distal end 137; however, in some embodiments such as that shown in FIG. 2A, the tendons 140 may be attached to only one of the proximal end 131 and the distal end 137 (e.g., only the distal end 137, such as to allow for articulation of an articulable region 138 near the distal end 137). The tendons 140 are shown as equally spaced apart, though as described above, in some embodiments, the tendons 140 may be unequally spaced apart. Additionally or alternatively, although the intermediate member 130 shown in FIG. 3 includes two tendons 140, in some embodiments the intermediate member 130 may include three, four, five, six, seven, eight, or more than eight tendons 140.

However, in some embodiments, one or more tendons 140 may have a varying cross-section (e.g., width) along their length. For example, a tendon 140 may have a wider width (e.g., as measured circumferentially in arc length around the intermediate member) at one longitudinal location, compared to its width at another longitudinal location. A wider portion of the tendon 140 may, in some embodiments, function as a spacer between adjacent tendons 140, to help prevent adjacent tendons 140 from buckling in a tangential direction (e.g., when pushed). However, the intermediate member 130 may include one or more spacers that are implemented in any suitable manner.

Figure 4:
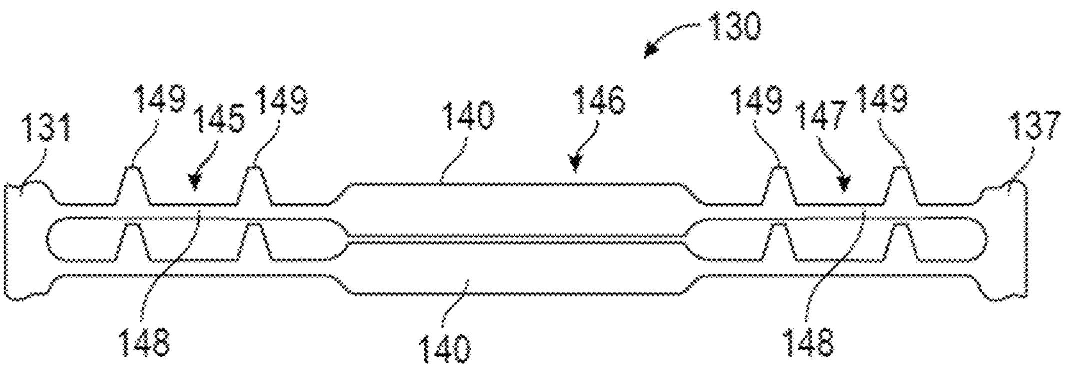
FIG. 4 depicts an unwrapped view of an example tube with tendons in an example steerable tube assembly, in accordance with the present technology.

For example, FIG. 4 illustrates an example portion of an intermediate member 130 including two adjacent tendons 140 in an unrolled condition. Each tendon 140 includes a first segment 145, a second segment 146, and a third segment 147 that are arranged end-to-end along the tendon 140. In the second segment 146, adjacent tendons 140 are nearly touching each other in the tangential direction such that only a narrow slot is present between the adjacent tendons 140 and has a width just sufficient to allow independent movement of each tendon 140. The narrow slot may, for example, be formed by removal of material such as laser cutting, where the width of the slot corresponds to the width of the laser beam.

In the first segment 145 and the third segment 147, each tendon 140 includes a flexible portion 148 and one or more spacers 149. The flexible portion 148 has a narrower width than the second segment 146 and narrower width than the spacer(s) 149, such that there is a wider gap between adjacent tendons 140. The one or more spacers 149 extend in a tangential direction and may be almost completely bridging the gap between adjacent flexible portions 148 in adjacent tendons 140. The spacer(s) 149 may function to suppress the tendency of the tendons 140 to shift in a tangential direction, thus improving control of the tendons 140 in a tangential direction during actuation of the tendons 140, thereby leading to more control in articulating the articulable region(s) of the steerable tube assembly. The exact shape of the spacer(s) 149 may vary. For example, as shown in FIG. 4 the spacers 149 may have a generally triangular shape, but may alternatively have any suitable shape (e.g., rectangular, semi-circular, etc.). In some embodiments, the spacers 149 may be integrally formed with one or more tendons 140.

Figure 7:
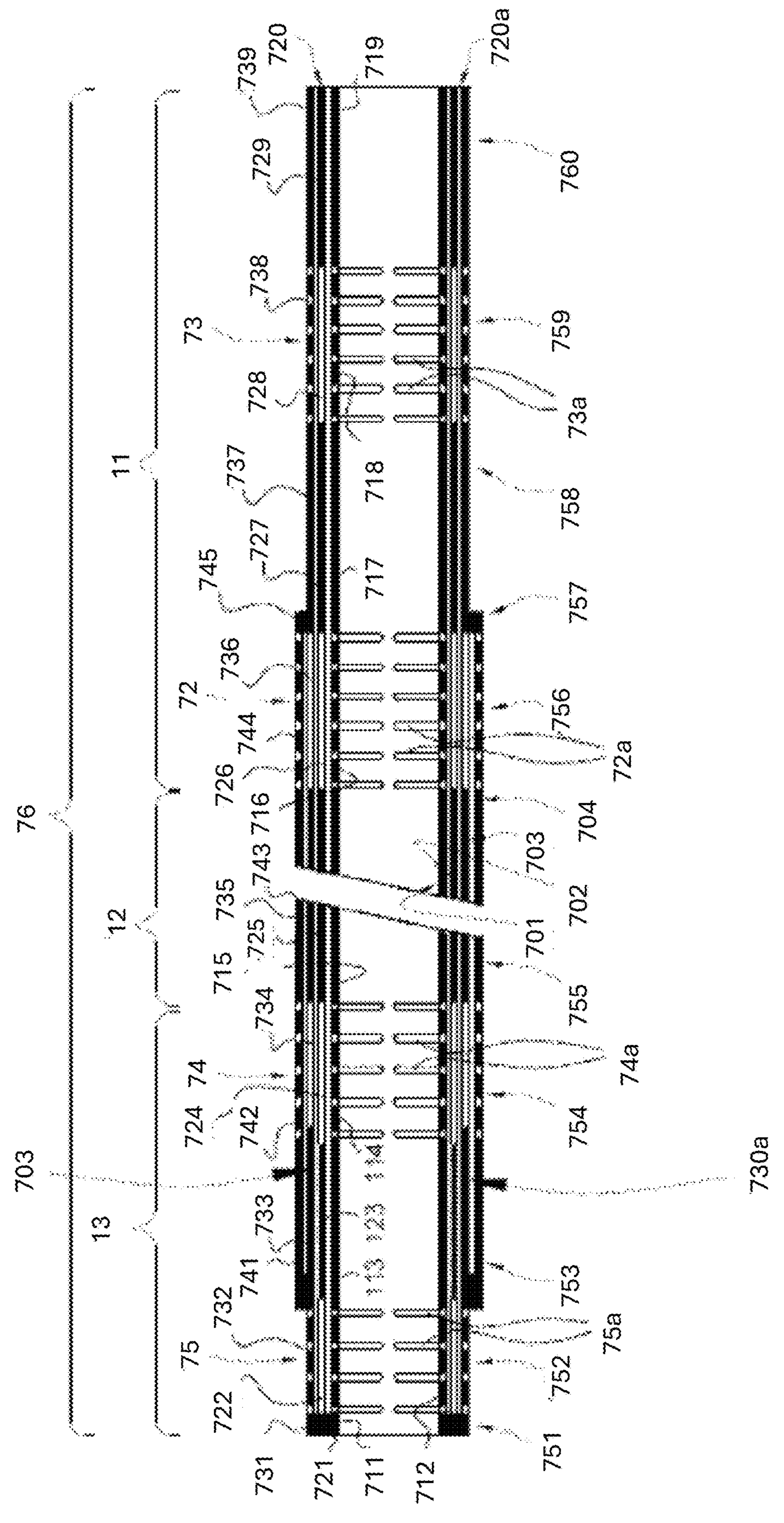
FIG. 7 shows a cross-sectional view of the example invasive instrument shown in FIG. 6, in accordance with the present technology.
Figure 8:
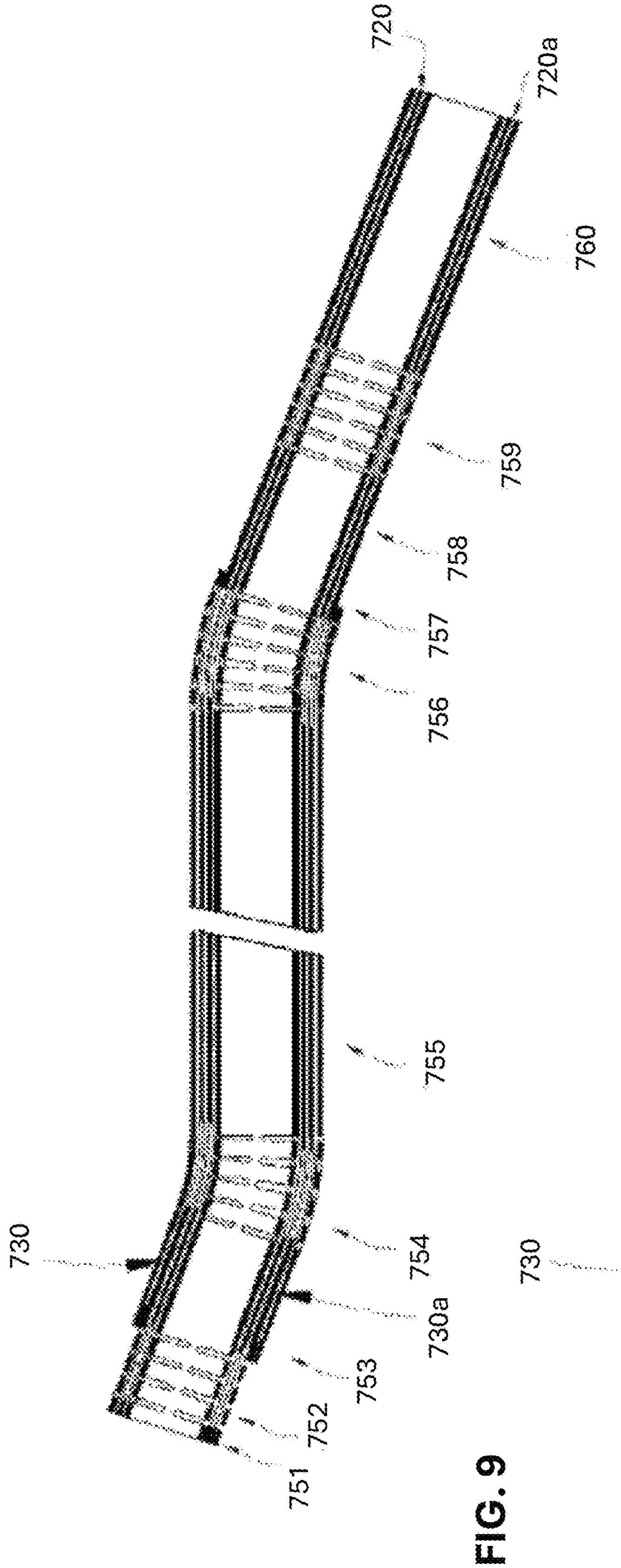
FIGS. 8 and 9 show examples of how the invasive instrument of FIGS. 6 and 7 can bend.
Figure 9:
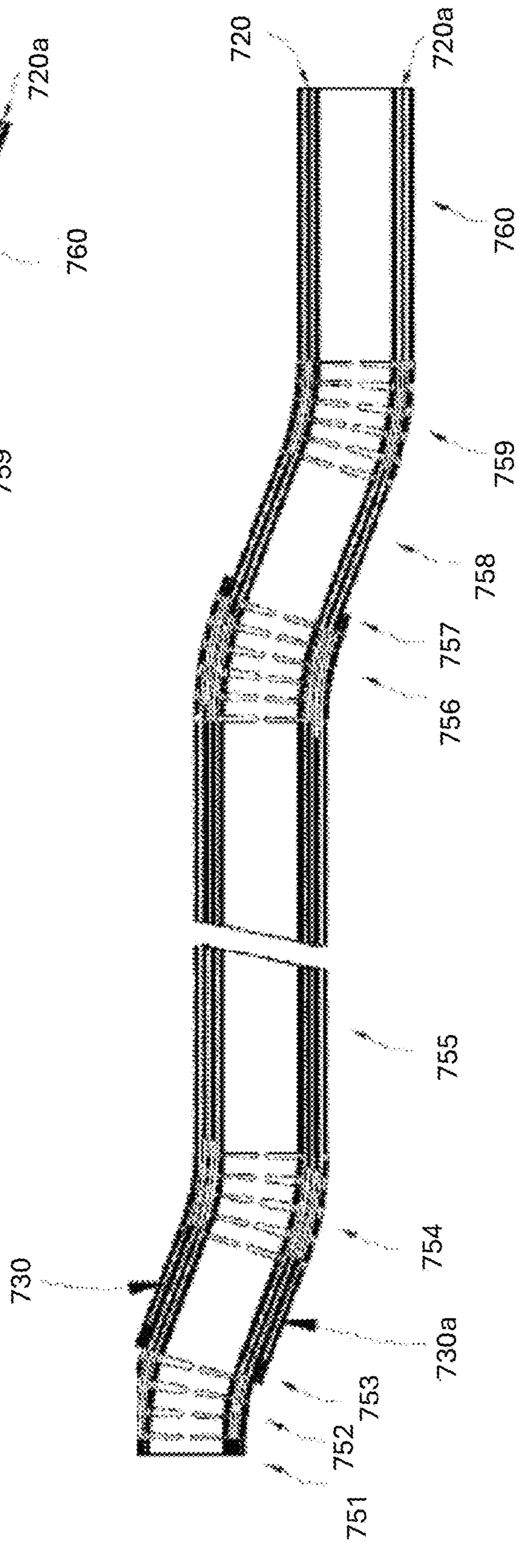
Figure 13:
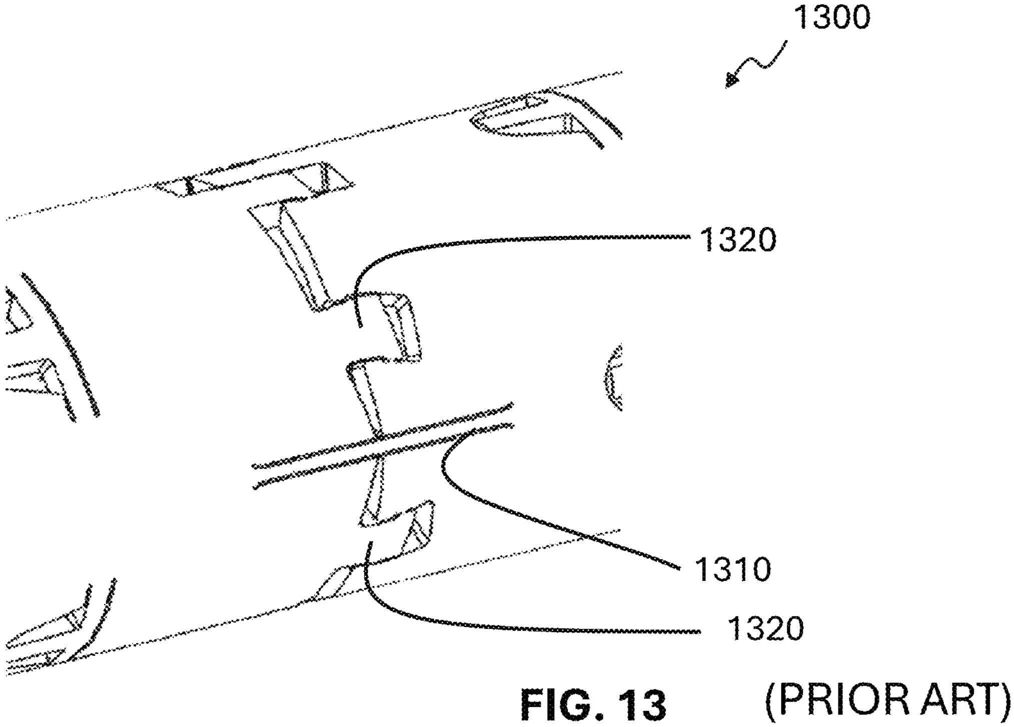
FIG. 13 (PRIOR ART)
Figure 14A:
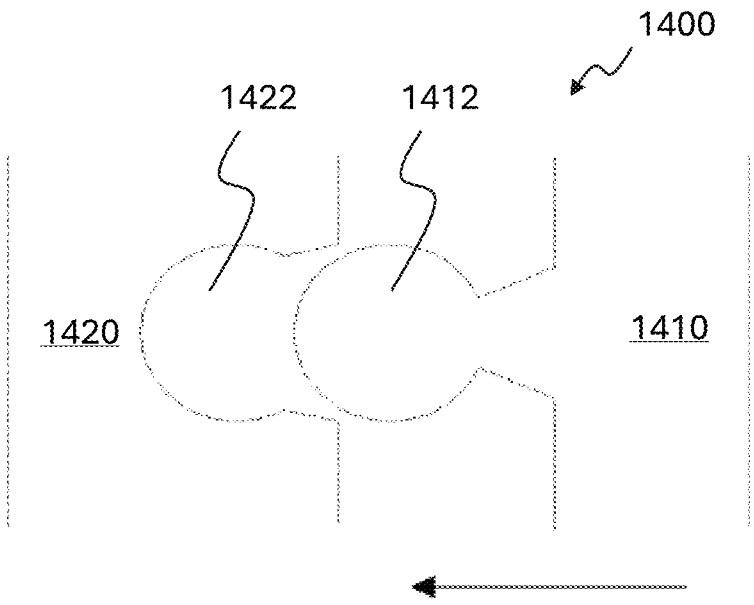
FIGS. 14A-22B show example playless hinge structures, in accordance with the present technology.
Figure 14B:
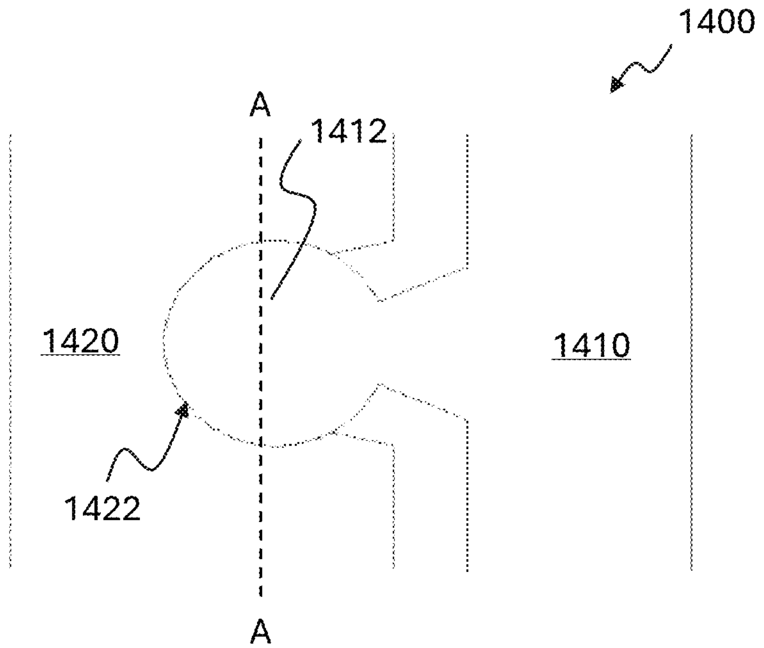
Figure 15:
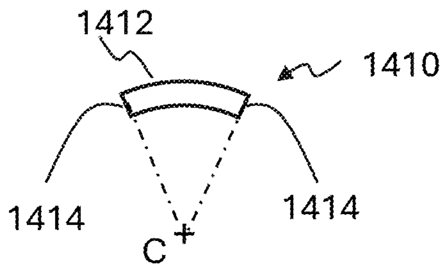
Figure 16:
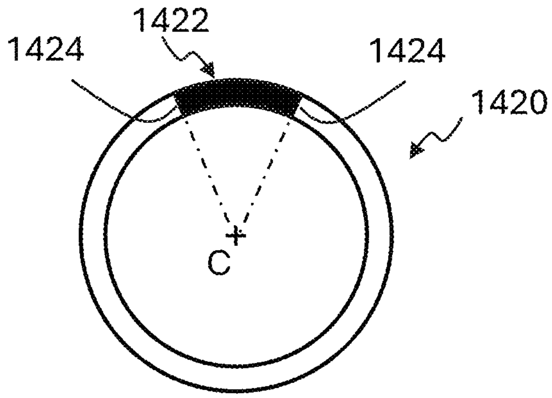
Figure 17:
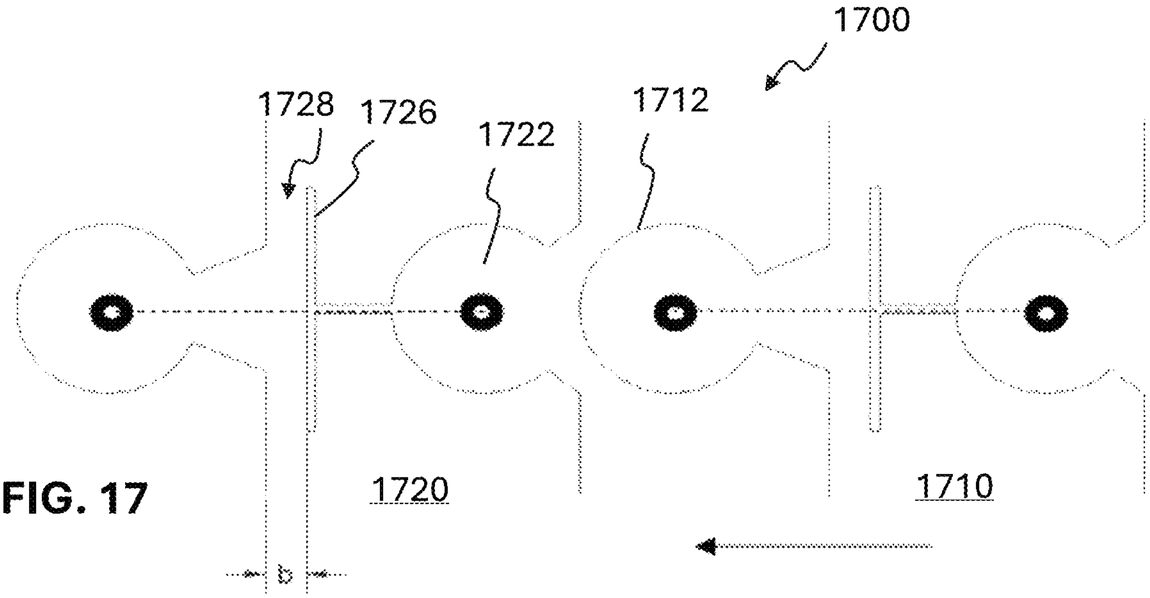

The intermediate member 130 may include any suitable spacers and/or other features, such as those described in FIGS. 4-16 of International Patent Application Publication No. WO2009/112060, FIGS. 6-10B of International Patent Application Publication No. WO2017/082720, FIGS. 15-17 of International Patent Application Publication No. WO2018/067004, FIGS. 5A-10 of International Patent Application Publication No. WO201/9009710, FIGS. 11E-14B, 17B, and 19A-20D of International Patent Application Publication No. WO2020080938, FIG. 9B of International Patent Application Publication No. WO2020/214027, FIGS. 10-19 of International Patent Application Publication No. WO2023/113598, or several figures in International Patent Application Publication No. WO2023/287289 and International Patent Application Publication No. WO2025026670, each of which is incorporated in its entirety herein by this reference.

The inner member 110, intermediate member 130, and/or outer member 150 may be formed from any suitable rigid material such as stainless steel, cobalt-chromium, shape memory alloy such as Nitinol®, plastic, polymer, composites and/or other materials. Additionally or alternatively, the elongate member(s) (e.g., inner member 110, intermediate member 130, and/or outer member 150) can be made by a 3D printing process or other known material deposition processes.

In some embodiments, various features of the elongate members (e.g., inner member 110, intermediate member 130, and/or outer member 150) of the steerable tube assembly (e.g., articulable regions, tendons, sliders, slots, spacers, etc.) may be formed through removal of material from the wall of each respective tube forming the members of the steerable tube assembly. For example, starting from a cylindrical tube with desired inner and outer diameters (and desired wall thickness), various features of an elongate member (e.g., inner member 110, intermediate member 130, outer member 150) may be formed by removing parts of the wall of the cylindrical tube, such as by laser cutting or water cutting. However, in some embodiments the elongate members may be formed through injection molding, plating techniques, 3D printing or other material deposition process, photochemical etching, deep pressing, conventional chipping techniques such as drilling or milling, and/or any suitable technique. In some embodiments, removal of material may be performed through laser cutting, which may allow for a very accurate and clean removal of material under reasonable economic conditions. In some embodiments, forming each elongate member (e.g., inner member, intermediate member, outer member) of the articulable tube assembly from a respective tube (e.g., metal tube, such as stainless steel) may enable each separate elongate member to maintain a relatively stable tubular form (e.g., flexible, but manipulable similar to a solid tube). With the elongate members being easily handled, they can be more easily assembled (e.g., nested within each other in a telescopic or concentric manner) into the articulable tube assembly.

The above-mentioned processes may be convenient ways to form each of the inner member 110, the intermediate member 130, and/or the outer member 150 in one overall process, without requiring additional steps for connecting different features of each elongate member. This simplified manufacturing process is advantageously contrasted from multiple steps that are required in manufacturing conventional steerable instruments such as with conventional steering cables, as steering cables must be connected in some way at end regions of a steerable catheter.

The inner and/or outer diameters of the members 110, 130, 150 may be selected such that at any given location along the assembled steerable tube assembly 100, the outer diameter of the inner member 110 is slightly less than the inner diameter of the intermediate member 130, the outer diameter of the intermediate member 130 is slightly less than the inner diameter of the outer member 150, in such a way that a sliding movement of the adjacent members with respect to each other is possible. The dimensioning should be such that a sliding fit is provided between adjacent elongate members. A clearance between adjacent elongate member may generally be in the order of 0.02 to 0.1 mm, but may depend on the specific application and material used. The clearance may be smaller than a wall thickness of the tendons 140 to prevent an overlapping configuration thereof. Restricting the clearance to about 30% to 40% of the wall thickness of the tendons 140 may, for example, be generally sufficient.

Specific dimensions and features of the members 110, 130, and 150 (and/or other elongate members) may vary depending on the application in which the steerable tube assembly may be used. For example, the steerable tube assembly may have a longer flexible portion which may help facilitate the use of the steerable tube assembly in areas of a human body that are navigable in tortuous spaces (e.g., colon, esophagus, curved blood vessels, etc.).

Additional examples of steerable tube assemblies and/or portions thereof are described in further detail in FIGS. 6-10.

Figure 6:
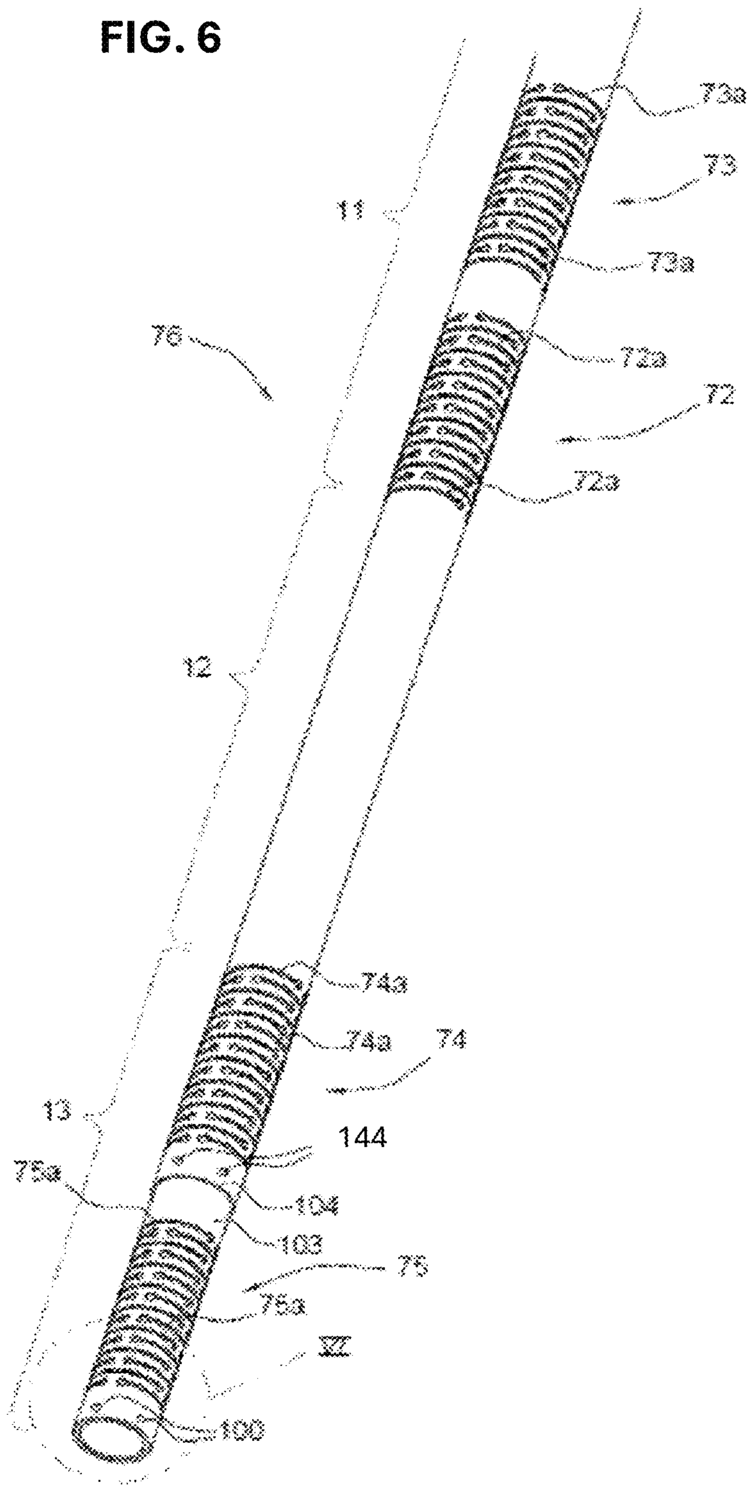
FIG. 6 shows an outside view of an example steerable invasive instrument having two steerable bendable distal end portions and two proximal flexible control portions, in accordance with the present technology.

FIG. 6 provides a detailed perspective view of the distal portion of an example embodiment of an elongated tubular body 76 of a steerable instrument which has two steerable distal bendable zones 74, 75 which are operated by two bendable proximal zones 72, 73, respectively. FIG. 6 shows that the elongated tubular body 76 comprises a number of co-axially arranged layers or cylindrical elements including an outer cylindrical element 104 (an example of outer member 150) that ends after a first distal articulable zone 74 at a distal end portion 13. The distal end portion 13 of the outer cylindrical element 104 is fixedly attached to a cylindrical element 103 located inside of and adjacent to the outer cylindrical element 104, e.g. by means of spot welding at welding spots 144. However, any other suitable attachment method can be used, including any mechanical snap fit connection or gluing by a suitable glue.

The elongated tubular body 76 as shown in FIG. 6 comprises four cylindrical elements in total, including two intermediate cylindrical elements 103 and 104 in which the steering members of the steering arrangement are arranged. However, additional or fewer cylindrical elements (e.g., tubular members) may be provided if desired.

The steering arrangement in the example embodiment of the elongated tubular body 76 as shown in FIG. 6 comprises the two flexible zones 72, 73 at the proximal end part 11 of the elongated tubular body 76, the two flexible zones 74, 75 at the distal end part 13 of the elongated tubular body 76, and the tendons that are arranged between related flexible zones at the proximal 11 and distal 13 end parts. An example actual arrangement of the tendons is shown in FIG. 7, which provides a schematic longitudinal cross-sectional view of the example embodiment of the elongated tubular body 76 as shown in FIG. 6.

Flexible zones 72, 73, 74, and 75 are, in this embodiment, implemented by providing the respective cylindrical elements with slits 72*a*, 73*a*, 74*a*, and 75*a*, respectively. Such slits 72*a*, 73*a*, 74*a*, and 75*a* may be arranged in any suitable pattern such that the flexible zones 72, 73, 74, and 75 have a desired flexibility in the longitudinal and tangential direction in accordance with a desired design.

FIG. 7 shows a longitudinal cross section of the four layers or cylindrical elements mentioned above, here indicated as the inner cylindrical element 701, the first intermediate cylindrical element 702, the second intermediate cylindrical element 703, and the outer cylindrical element 704.

The inner cylindrical element 701, as seen along its length from the distal end to the proximal end of the instrument, comprises a rigid ring 711, which is arranged at the distal end part 13 of the steerable instrument, a first flexible portion 712, a first intermediate rigid portion 713, a second flexible portion 714, a second intermediate rigid portion 715, a third flexible portion 716, a third intermediate rigid portion 717, a fourth flexible portion 718, and a rigid end portion 719, which is arranged at the proximal end portion 11 of the steerable instrument.

The first intermediate cylindrical element 702, as seen along its length from the distal end to the proximal end of the instrument, comprises a rigid ring 721, a first flexible portion 722, a first intermediate rigid portion 723, a second flexible portion 724, a second intermediate rigid portion 725, a third flexible portion 726, a third intermediate rigid portion 727, a fourth flexible portion 728, and a rigid end portion 729. The portions 722, 723, 724, 725, 726, 727 and 728 together form a longitudinal tendon 720 (an example of tendon 140) that can be moved in the longitudinal direction. The longitudinal dimensions of the rigid ring 721, the first flexible portion 722, the first intermediate rigid portion 723, the second flexible portion 724, the second intermediate rigid portion 725, the third flexible portion 726, the third intermediate rigid portion 727, the fourth flexible portion 728, and the rigid end portion 729 of the first intermediate element 702, respectively, are aligned with, and may be approximately equal to the longitudinal dimensions of the rigid ring 711, the first flexible portion 712, the first intermediate rigid portion 713, the second flexible portion 714, the second intermediate rigid portion 715, the third flexible portion 716, the third intermediate rigid portion 717, the fourth flexible portion 718, and the rigid end portion 719 of the inner cylindrical element 701, respectively, and are coinciding with these portions as well. In this description "approximately equal" means that respective same dimensions are equal within a margin of less than 10%, such as less than 5%.

Similarly, the first intermediate cylindrical element 702 comprises one or more other tendons of which one is shown with reference number 720*a*.

The second intermediate cylindrical element 703, as seen along its length from the distal end to the proximal end of the instrument, comprises a first rigid ring 731, a first flexible portion 732, a second rigid ring 733, a second flexible portion 734, a first intermediate rigid portion 735, a first intermediate flexible portion 736, a second intermediate rigid portion 737, a second intermediate flexible portion 738, and a rigid end portion 739. The portions 733, 734, 735 and 736 together form a tendon 730 (an example of tendon 140) that can be moved in the longitudinal direction. The longitudinal dimensions of the first rigid ring 731, the first flexible portion 732 together with the second rigid ring 733 and the second flexible portion 734, the first intermediate rigid portion 735, the first intermediate flexible portion 736, the second intermediate rigid portion 737, the second intermediate flexible portion 738, and the rigid end portion 739 of the second intermediate cylinder 703, respectively, are aligned with, and may be approximately equal to the longitudinal dimensions of the rigid ring 711, the first flexible portion 712, the first intermediate rigid portion 713, the second flexible portion 714, the second intermediate rigid portion 715, the third flexible portion 716, the third intermediate rigid portion 717, the fourth flexible portion 718, and the rigid end portion 719 of the first intermediate element 702, respectively, and are coinciding with these portions as well.

Similarly, the second intermediate cylindrical element 703 comprises one or more other tendons of which one is shown with reference number 730*a*.

The outer cylindrical element 704, as seen along its length from the distal end to the proximal end of the instrument, comprises a first rigid ring 741, a first flexible portion 742, a first intermediate rigid portion 743, a second flexible portion 744, and a second rigid ring 745. The longitudinal dimensions of the first flexible portion 742, the first intermediate rigid portion 743 and the second flexible portion 744 of the outer cylindrical element 704, respectively, are aligned with, and may be approximately equal to the longitudinal dimension of the second flexible portion 734, the first intermediate rigid portion 735 and the first intermediate flexible portion 736 of the second intermediate element 703, respectively, and are coinciding with these portions as well. The rigid ring 741 has approximately the same length as the rigid ring 733 and is fixedly attached thereto, e.g. by spot welding or gluing. The rigid ring 745 may overlap with the second intermediate rigid portion 737 only over a length that is required to make an adequate fixed attachment between the rigid ring 745 and the second intermediate rigid portion 737, respectively, e.g. by spot welding or gluing. The rigid rings 711, 721 and 731 are attached to each other, e.g., by spot welding or gluing. This may be done at the end edges thereof but also at a distance of these end edges.

In some embodiments, the same may apply to the rigid end portions 719, 729 and 739, which can be attached to one another as well in a comparable manner. However, the construction may be such that the diameter of the cylindrical elements at the proximal portion is larger, or smaller, with respect to the diameter at the distal portion. In such an embodiment the construction at the proximal portion differs from the one shown in FIG. 7. As a result of the increase or decrease in diameter an amplification or attenuation is achieved, i.e., the bending angle of a flexible zone at the distal portion will be larger or smaller than the bending angle of a corresponding flexible portion at the proximal portion.

The inner and outer diameters of the cylindrical elements 701, 702, 703, and 704 are chosen in such a way at a same location along the elongated tubular body 76 that the outer diameter of inner cylindrical element 701 is slightly less than the inner diameter of the first intermediate cylindrical element 702, the outer diameter of the first intermediate cylindrical element 702 is slightly less than the inner diameter of the second intermediate cylindrical element 703 and the outer diameter of the second intermediate cylindrical element 103 is slightly less than the inner diameter of the outer cylindrical element 704, in such a way that a sliding movement of the adjacent cylindrical elements with respect to each other is possible. The dimensioning should be such that a sliding fit is provided between adjacent elements. A clearance between adjacent elements may generally be in the order of 0.02 to 0.1 mm, but depends on the specific application and material used. The clearance may be smaller than a wall thickness of the tendons to prevent an overlapping configuration thereof. Restricting the clearance to about 30% to 40% of the wall thickness of the tendons is generally sufficient.

As can be seen in FIG. 7, flexible zone 72 of the proximal end part 11 is connected to the flexible zone 74 of the distal end part 13 by portions 734, 735 and 736, of the second intermediate cylindrical element 703, which form a first set of longitudinal steering elements of the steering arrangement of the steerable instrument. Furthermore, flexible zone 73 of the proximal end part 11 is connected to the flexible zone 75 of the distal end part 13 by portions 722, 723, 724, 725, 726, 727, and 728 of the first intermediate cylindrical element 702, which form a second set of tendons of the steering arrangement. The use of the construction as described above allows the steerable instrument 10 to be used for double bending. The working principle of this construction will be explained with respect to the examples shown in FIGS. 8 and 9.

For the sake of convenience, as shown in FIGS. 7, 8, and 9, the different portions of the cylindrical elements 701, 702, 703, and 704 have been grouped into zones 751-760 that are defined as follows. Zone 751 comprises the rigid rings 711, 721, and 731. Zone 752 comprises the portions 712, 722, and 732. Zone 753 comprises the rigid rings 733 and 741 and the portions 713 and 723. Zone 754 comprises the portions 714, 724, 734 and 742. Zone 755 comprises the portions 715, 725, 735 and 743. Zone 756 comprises the portions 716, 726, 736 and 744. Zone 757 comprises the rigid ring 745 and the parts of the portions 717, 727, and 737 coinciding therewith. Zone 758 comprises the parts of the portions 717, 727, and 737 outside zone 757. Zone 759 comprises the portions 718, 728 and 738. Finally, zone 760 comprises the rigid end portions 719, 729 and 739.

In order to deflect at least a part of the distal end part 13 of the steerable instrument, it is possible to apply a bending force, in any radial direction, to zone 758. According to the examples shown in FIGS. 8 and 9, zone 758 is bent downwards with respect to zone 755. Consequently, zone 756 is bent downwards. Because of the first set of tendons comprising portions 734, 735, and 736 of the second intermediate cylindrical element 703 that are arranged between the second intermediate rigid portion 737 and the second rigid ring 733, the downward bending of zone 756 is transferred by a longitudinal displacement of the first set of tendons into an upward bending of zone 754 with respect to zone 755. This is shown in both FIGS. 8 and 9.

It is to be noted that the example downward bending of zone 756 only results in the upward bending of zone 154 at the distal end of the instrument as shown in FIG. 8. Bending of zone 752 as a result of the bending of zone 756 is prevented by zone 753 that is arranged between zones 752 and 754. When subsequently a bending force, in any radial direction, is applied to the zone 760, zone 759 is also bent. As shown in FIG. 9, zone 760 is bent in an upward direction with respect to its position shown in FIG. 8. Consequently, zone 759 is bent in an upward direction. Because of the second set of tendons comprising portions 722, 723, 724, 725, 726, 727 and 728 of the first intermediate cylindrical element 702 that are arranged between the rigid ring 721 and the rigid end portion 729, the upward bending of zone 759 is transferred by a longitudinal displacement of the second set of tendons into a downward bending of zone 752 with respect to its position shown in FIG. 8.

FIG. 9 further shows that the initial bending of the instrument in zone 754 as shown in FIG. 8 will be maintained because this bending is only governed by the bending of zone 756, whereas the bending of zone 752 is only governed by the bending of zone 759 as described above. Due to the fact that zones 752 and 754 are bendable independently with respect to each other, it is possible to give the distal end part 13 of the steerable instrument a position and longitudinal axis direction that are independent from each other. In particular the distal end part 13 can assume an advantageous S-like shape. The skilled person will appreciate that the capability to independently bend zones 752 and 754 with respect to each other, significantly enhances the maneuverability of the distal end part 13 and therefore of the steerable instrument as a whole.

Obviously, it is possible to vary the lengths of the flexible portions shown in FIGS. 7, 8, and 9 as to accommodate specific requirements with regard to bending radii and total lengths of the distal end part 13 and the proximal end part 11 of the steerable instrument or to accommodate amplification or attenuation ratios between bending of at least a part of the proximal end part 11 and at least a part of the distal end part 13.

In the shown embodiment, the tendons comprise one or more sets of tendons that form integral parts of the one or more intermediate cylindrical elements 702, 703. For example, the tendons may comprise remaining parts of the wall of an intermediate cylindrical element 702, 703 after the wall of the intermediate cylindrical element 702, 703 has been provided with longitudinal slits that define the remaining tendons.

Figure 10:
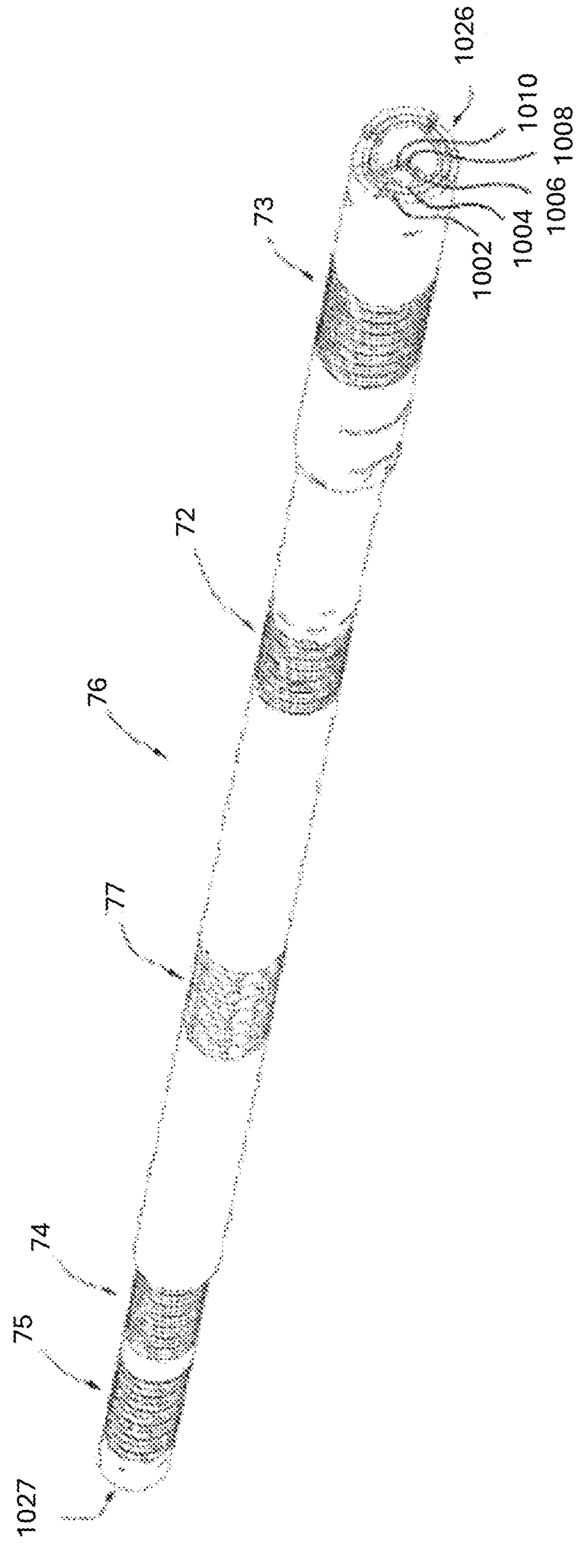
FIG. 10 shows an example embodiment of the invasive instrument shown in FIGS. 6-9, wherein at least a portion of an intermediate section between the distal end and the proximal end is flexible too, in accordance with the present technology.

FIG. 10 shows a 3D view of an example of a steerable instrument. Like reference numbers refer to the same elements as in other figures. Their explanation is not repeated here. The instruments comprises five coaxial cylindrical elements 1002-1010. An inner cylindrical element 1010 is surrounded by intermediate cylindrical element 1008 which is surrounded by intermediate cylindrical element 1006 which is surrounded by intermediate cylindrical element 1004 which is, finally surrounded by outer cylindrical element 1002. Inner intermediate cylindrical element may be made of a flexible spiraling spring. The proximal and distal ends, respectively, of the instrument are indicated with reference numbers 1026 and 1027, respectively.

As shown, here, instrument 76 comprises a flexible zone 77 in its intermediate part between flexible zone 72 and flexible zone 74. For example, intermediate cylindrical element 204 (which is located at the outer side in the area of flexible zone 77) may be provided with a slotted structure to provide intermediate cylindrical element with a desired flexibility. The longitudinal length of the slotted structure in flexible zone 77 depends on the desired application. It may be as long as the entire part between flexible zones 72 and 74. All other cylindrical elements 1006, 1008, 1010 inside intermediate cylindrical element 1004 are also flexible in flexible zone 77. Those cylindrical elements that have tendons in the flexible zone 77 are flexible by way of definition. Others are provided with suitable hinges, such as made by suitable slotted structures.

Some locations to be operated in a body need specifically designed instruments. For example, by making the intermediate part 12 of the instrument completely flexible, the instrument can also be used in areas in the body which are only accessible via curved natural access guides/channels, like the colon, the stomach via the oesophagus or the heart via curved blood vessels. Additionally or alternatively, the wall thickness of cylindrical elements may depend on the application of the resulting tube assembly. For medical applications the wall thickness may, for example be in a range of 0.03-2.0 mm, 0.03-1.0 mm, 0.05-0.5 mm, or 0.08-0.4 mm. Additionally or alternatively, the diameter of cylindrical elements may depend on the application of the resulting assembly. For medical applications the diameter may be in a range of 0.5-20 mm, 0.5-10 mm, or 0.5-6 mm.

II. Prior Hinge Designs

In mechanical mechanisms like steerable instruments, the management of play between parts is a critical factor in obtaining optimum performance. Play has a direct influence on, for example, friction, movements, and positioning accuracy. When steerable instruments are made conventionally from separate parts that will be assembled after part manufacturing, play can be managed by defining the correct dimensions of these parts and allowable tolerances. During assembly one can also adjust positions of parts with respect to each other and fix them in place to set a desired amount of play.

In some embodiments, as described above, a steerable tube assembly may include tubular members that are created, in a pre-assembled state, by removing material out of a tube's wall in a predetermined pattern. This process may result in features such as tendons (e.g., tendons 140) and hinges (e.g., in articulable regions) that are separated by an amount of play created by the material removal process, where such play has a minimum width equal to or larger than the width of the cutting implement (for example the laser cutting beam). This play can have disadvantages for the product performance. For example, when a steerable instrument is made with multiple hinges in the articulable regions, the play per hinge times the number of hinges over the length of the instrument might result in an unacceptable total play in the instrument, both in the longitudinal and tangential (circumferential) direction of the instrument.

Figure 11A:
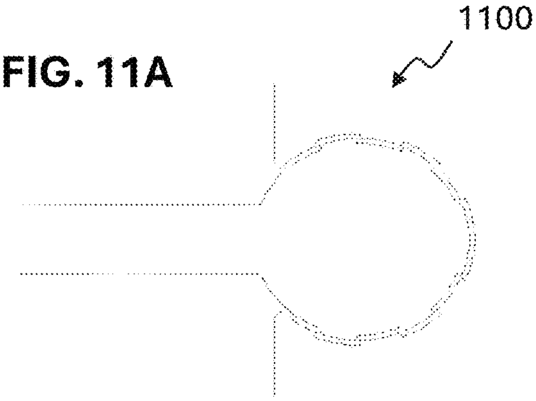
FIGS. 11A-13 show examples of prior art hinge structures.
Figure 11B:
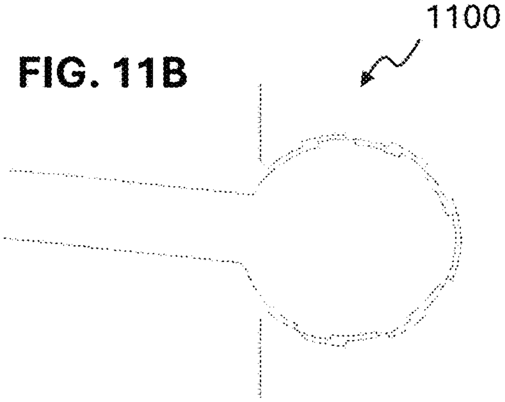
(PRIOR ART) FIG. 11B

While there are some existing hinge designs for such steerable instruments, they may still have some drawbacks. For example, some prior hinge designs are configured to optimize play reduction at a certain degree of bending (e.g., minimize spacing in the hinge to be much smaller than the minimum slot width between tendons attainable by a laser beam used to make a laser cut pattern in the hinge, such as zero or close to zero spacing). FIGS. 11A and 11B depict an example of a prior hinge 1100 as shown and described in PCT International Appl. Publication No. WO 2023/287286 (which is incorporated herein in its entirety) in which opposing circular surfaces in a hinge have serrated surfaces in the form of a block wave pattern. FIG. 11A shows the hinge directly after the laser cutting process in which the distance between opposing surfaces is equal to the width of the used laser beam. Thus, the play equals the width of the used laser beam. However, when rotating the opposed surfaces relative to one another the extending portions of the circular surfaces move to a position where they are opposite and the play between them, and thus in the hinge, reduces seriously, as shown in FIG. 11B. A disadvantage of this solution is that in the neutral, as cut, configuration (FIG. 611A) the hinge still has some play. Moreover, the movement of surfaces of the hinge is not smooth due to the serrated hinge surface. In a situation with side forces, in which the center points of the two circular surfaces do no longer coincide, the hinge could even lock up.

Figure 12A:
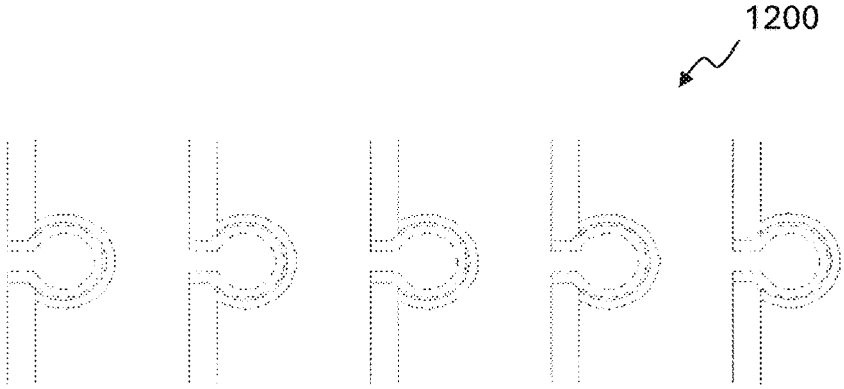
(PRIOR ART) FIG. 12A
Figure 12B:
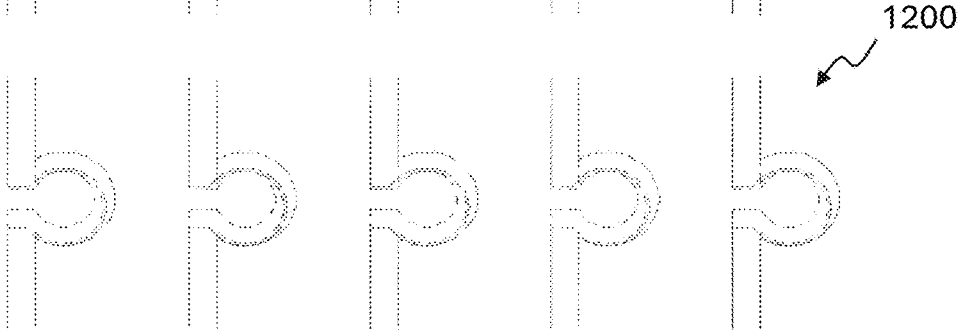

FIGS. 12A and 12B show another example of a prior hinge 1200 known from WO2023287286, in which two layers of tubing are cut with hinges. FIG. 12A shows two layers of tubing, as cut. The outer tube is shown in solid lines and the inner tube in dashed lines. Directly after cutting, the circular surfaces of the inner and outer tubes are all aligned such that they have center points on a line also crossing a center line of the tubes. By tangential displacement of one tube with respect to the other and then fix in place by for example laser welding, as shown in FIG. 12B, the tangential play may be reduced, such as to a value equal or close to zero, or at least smaller than the width of the original slots made by a laser beam. However, a longitudinal play still exists. Additionally or alternatively, one tube in the longitudinal direction may be displaced in a longitudinal direction and then fixed in place by attaching the circular surfaces of the inner and outer tubes to one another (e.g., by laser welding). In this configuration, however, tangential play would still exist. Furthermore, this solution requires two coaxial tubes and one would still have play in a tangential and/or longitudinal direction.

As another example, a method for reducing play is utilizing a hinge that rotates based on elastic deformation. An example of a such a hinge 1300 is shown in FIG. 13. Theoretically, one could design a hinge such that at known maximum longitudinal and tangential loads, the hinge experiences no play. However, in practice, such a hinge may be too stiff to bend and would result in a badly steerable instrument. In the example shown in FIG. 13, the elastic hinge is designed with adjacent hinge portions that can rotate relative to one another in a plane perpendicular to a center axis. Adjacent portions are attached to one another by two small, flexible bridges 1310 located at positions 180 degrees rotated as seen in the tangential direction. The centers of these two bridges form points of rotation, and by properly designing these bridges, adjacent hinge portions can rotate easily relative to one another. Because of the two attaching bridges 1310, the hinge shown in FIG. 13 has no play in the longitudinal direction between adjacent hinge portions (as relative longitudinal movement between adjacent hinge portions is limited by the bridges 1310. To help reduce tangential play, the hinge 1300 further includes two 'ears' or extensions 1320 positioned at tangentially equidistant locations from each bridge, such that at slight rotation of hinge 1300, the extensions 1320 of one hinge portion touch surfaces of an opposing hinge portion and therefore eliminate tangential play. However, the hinge 1300 may be relatively stiff, and may still have unacceptable amounts of play within certain ranges of bending motion (e.g., in a neutral or straight articulated shape).

III. Playless Hinges

It is an object of the present technology to provide a tube with a hinge which can be used in an articulable device, such as a steerable instrument or other steerable medical device, such as for endoscopic, open, and/or invasive type of applications where the hinge has reduced play without sacrificing performance such as flexibility, range of motion, etc. For example, in some embodiments a steerable tube may include an elongated tubular member including a first hinge portion and a second hinge portion formed in a wall of the tubular member. The first hinge portion may include a hinge extension having a first arcuate articulating edge, and the second hinge portion may include a hinge recess having a second arcuate articulating edge, where the hinge extension is received in the hinge recess such that the first and second arcuate articulating edges are engaged to thereby couple the first and second hinge portions together in a snap-fit connection. For example, once the first and second hinge portions are coupled together, the hinge extension may articulate within the hinge recess, with the hinge extension and hinge recess operating similar to a ball and socket, respectively (e.g., in a two-dimensional manner).

Advantageously, a hinge including the first and second hinge portions may be formed in the same tubular member (e.g., any member with an articulable region such as articulable regions 118, 138, and 158), which may simplify the manufacturing process in that, for example, manufacture of a steerable tube including such a hinge does not require the assembly of many small, disparate parts. Rather, the wall material of the tubular member in which the first and second hinge portions are formed may help keep the first and second hinge portions in place (and aligned) relative to each other until final assembly (e.g., coupling of the hinge extension into the hinge recess, as further described in detail herein) is performed. Additionally, in some embodiments, the first and second hinge portions may be formed in a wall of the same tubular member via a cutting process such as laser cutting. In some of these embodiments, a laser beam may be directed radially inward toward a centerline of the tubular member, resulting in angled arcuate articulating edges (for the hinge extension and the hinge recess) that are profiled radially inward toward due to the curvature of the tubular member. The abutting interaction of angled cut surfaces between adjacent pieces also may help hold together the first and second hinge portions.

FIGS. 14A and 14B illustrate an example hinge 1400 in which the diameter of a protruding circular hinge extension 1412 of a first hinge portion 1410 is equal to the diameter of a hinge recess 1422 of an adjacent second hinge portion 1420, if one prefers zero play. In most applications, the first and second hinge portions have a ring shape and are symmetric in the tangential direction of the instrument. For example, the hinge may have an identical construction at the opposite side 180 degrees tangentially rotated; that is, two hinge extensions may be 180 degrees circumferentially offset from each other and two hinge recesses 180 degrees circumferentially offset from each other. To assemble the hinge 1400, the hinge extension (e.g., protruding partially circular part) of the first hinge portion 1410 may be clicked into the hinge recess of the second hinge portion 1420 by applying an assembly force indicated with an arrow. This can easily be done by for example sliding the tube in which all hinges are cut over a mandrel and then applying a sufficient amount of compressing force that results in a configuration as in FIG. 14B. The applied force may also be in the opposite direction or both hinge portions may be pushed towards one another.

In some embodiments, each of the hinge extension 1412 and the hinge recess 1422 may be formed by cutting or otherwise removing material from the same tubular member. For example, a wall of the tubular member may be cut with a laser beam in a laser cutting process. In this example, due to the curvature of the tubular member, the angle of the laser beam relative to the wall may be such that the laser beam is directed toward a center of the cross-section of the tubular member. For example, FIG. 15 illustrates a simplified schematic of a cross-sectional view of a first hinge portion 1410. As shown in FIG. 15, the hinge extension 1412 may be formed by directing a laser beam from outside the tubular member toward a center C of the tubular member, thereby cutting an articulating edge 1414 (which is arcuate when viewed tangentially) that is profiled or angled radially inward toward the center C. Similarly, FIG. 16 illustrates a simplified schematic of a cross-sectional view of a second hinge portion 1420. As shown in FIG. 16, the hinge recess 1422 may be formed by directing a laser beam from outside the tubular member toward a center C of the tubular member, thereby cutting an articulating edge 1424 (which is arcuate when viewed tangentially) that is profiled or angled radially inward toward the center C. In other words, the portions of the wall of the tubular member forming the hinge extension 1412 and the hinge recess 1422 as a result of laser cutting may have pie-shaped or wedge-shaped profiles due at least in part to the curvature of the laser cut tubular member. The radially angled surfaces of the articulating edges on the hinge extension and hinge recess may abut each other so as to help hold together the engagement between the hinge extension and the hinge recess.

In some embodiments, the hinge may be configured with additional feature(s) to improve the ability of the hinge recess to receive the hinge extension. For example, the hinge recess may include a slot pattern configured to improve the ability of the hinge recess to open and receive the hinge extension and/or the hinge extension may include a slot pattern configured to improve the ability of the hinge extension to compress and be received within the hinge recess.

For example, FIG. 17 illustrates an example hinge 1700 with a hinge recess including a slot pattern 1726. Hinge 1700 includes two adjacent hinge portions 1710 and 1720 (similar to first hinge portion 1410 and second hinge portion 1420, respectively), where a first hinge portion 1710 includes a hinge extension 1722 such as a protruding circular projection, and a second hinge portion 1720 includes a hinge recess 1722. The hinge extension 1712 has a center and the hinge recess 1722 has a center as well. In the shown example, a line-dotted in FIG. 17—connects these two centers as shown. The second hinge portion 1720 includes a first slot extending in a direction coinciding with the orientation of the line, and a second slot extending at an angle (e.g., 90 degrees) to the first slot. For example, the second hinge portion 1720 may include a slot pattern including a first slot and a second slot arranged in a "T"-shaped pattern as shown in FIG. 17, though the hinge 1700 may include any suitable slot pattern configured to improve the ability of the hinge recess to open (e.g., open tangentially). The first slot has a predetermined first length and the second slot has a predetermined second length. At one end the first slot is open to the hinge recess 1722 and at its other end the first is open to the second slot, such as at a center position of the second slot. The second hinge portion 1720 may further include a material strip 1728 with width b such that the second slot is located at a distance b from a side of the second hinge portion 1720 that includes a hinge extension for an adjacent hinge arrangement (with another adjacent hinge portion). In some embodiments, the maximum opening angle to open the recess 1722 is configured such that the maximum bending stress of the hinge portion 1710 (e.g., within the material strip 1728) is no greater than the fracture stress of the material of which the hinge portion 1710 is made. For example, the maximum opening angle to open the recess 1722 may be configured such that the maximum bending stress is less than the yield stress of the material of the hinge portion 1710. In some embodiments, the maximum bending stress of the hinge portion 1710 may be controlled at least in part by the dimensions of the material strip 1728 (e.g., the width b) and one or more aspects of the slot pattern 1726 (e.g., length of the second slot that is perpendicular to the center-to-center line connecting the center of the hinge extension 1712 and the center of the hinge recess 1722).

In some embodiments, the slot pattern of a hinge (e.g., hinge 1700) may function as a fiducial to help indicate one or more suitable weld spots or other locations for joining of adjacent elongate members (e.g., similar to weld spots 144 described with reference to FIG. 2B).

In this configuration, the required undercut can be designed at any desired proportion. To be able to assemble the hinges, the material strip width b can be designed such that the hinge recess 1722 readily opens or widens easily when a sufficient longitudinal assembly force, indicated with an arrow, is applied to the ring-shaped hinge portions. Of course, this force may be directed in the opposite direction or two forces may be applied, directed towards one another. Once the hinge projection 1712 is seated in the hinge recess 1722, one could apply a continued longitudinal force that helps closing the hinge recess 1722, even if the material strip 1728 was deformed plastically during opening of the hinge recess 1722.

Figure 18:
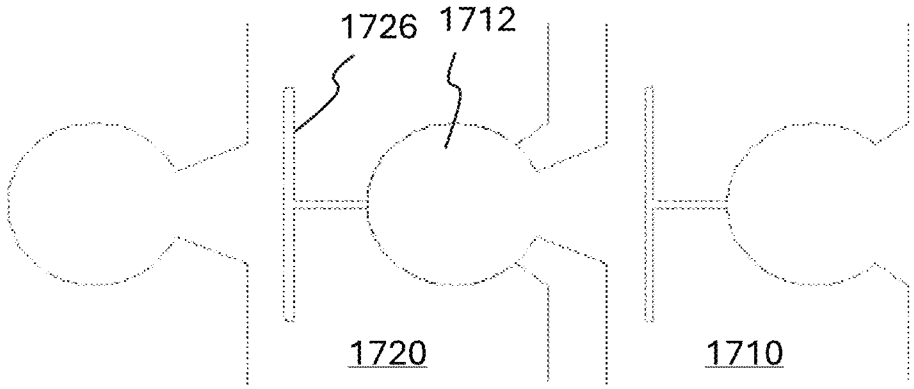

An example result of applying the assembly force to the hinge 1700 is shown in FIG. 18. Of course, many other slot patterns might be possible for achieving similar results. For example, the slot 1726 may include a second slot that is centered or not centered relative to the first slot. Additionally or alternatively, the slot 1726 may include a second slot that is angled at a non-perpendicular angle relative to the first slot. Additionally or alternatively, the slot 1726 may include a pattern of linear and/or curvilinear slots. Additionally or alternatively, length and width b and geometry of the bridge might vary, etc.

FIG. 18 shows an assembly of two adjacent hinge portions 1710 and 1720, where all hinge portions are positioned along one longitudinal line along the assembly length and one can understand how the opening of the hinge recesses 1726 works under longitudinal load. In practice, hinges may have more than two such hinge portions.

Figure 19:
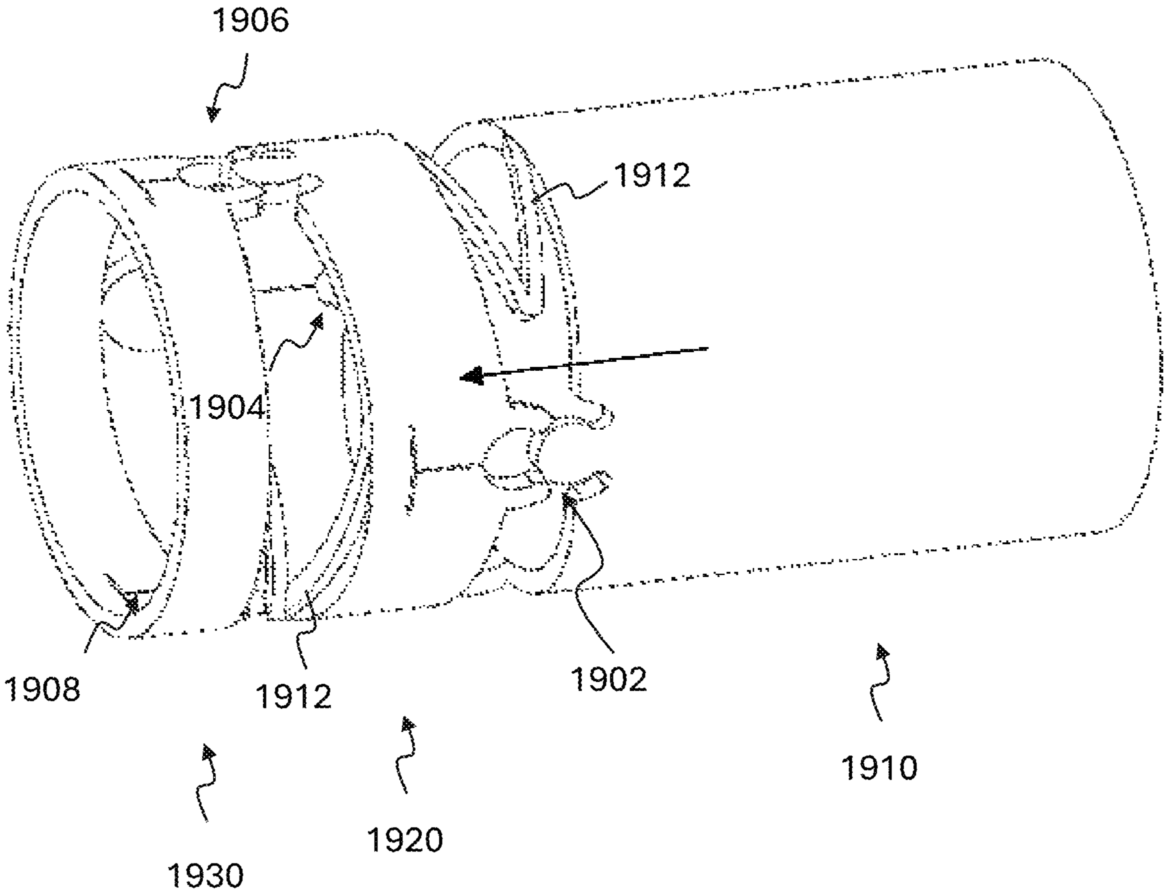

FIG. 19 is an example of a portion of a tube including multiple hinge structures similar to that shown in FIGS. 17 and 18. FIG. 19 shows a tube including three adjacent ring-shaped hinge portions in 3D form; however, a tube may include more than three hinge portions. In this example, consecutive sets of hinge extensions and hinge recesses are rotated about 90 degrees in the tangential direction at progressive longitudinal locations along the length of the tube (e.g., hinge structure 1906 relative to hinge structure 1902), to provide the hinge with the capacity to bend in all directions. All sets with one hinge extension and one hinge recess may form a snap-fit structure. Furthermore, as shown in FIG. 19, the tube may include multiple hinge structures arranged 180 degrees circumferentially offset from one another at one or more longitudinal locations along the length of the tube. For example, as shown in FIG. 19, hinge structures 1902 and 1904 may be arranged about 180 degrees circumferentially offset from one another, and hinge structures 1906 and 1908 may be arranged about 180 degrees circumferentially offset from one another.

In some embodiments, it might be difficult to design the hinge elements and the material strip dimension such that at an assembly compression force, the recesses still automatically open. This can be solved with elements like one or more flexible spring bridges connecting adjacent hinge portions, which may also help (at least temporarily) hold the hinge portions in approximate desired positions relative to each other until full assembly with compressive force. A set of spring bridges placed along the length of the tube between adjacent hinge portions in each hinge structure may, for example, help hold together the hinge portions in a desired configuration until and while a longitudinal compressive force is applied to the tube, thereby enabling the simultaneous assembly (coupling) of adjacent hinge portions across multiple hinge structures, without requiring separate assembly of each individual hinge structure. As such, the spring bridges may help simplify and increase the efficiency of the manufacturing process of a tube with such hinge structures. In some embodiments, such flexible spring bridges can be made during the same (laser) cutting process as used to make the rest of the hinge structure from the same tube FIG. 19 illustrates an example in which the spring bridges 1912 are V-shaped, with joined arms allowing for axial shortening in response to a longitudinal compressive force (e.g., the bridge may include a vertex between two arms that is oriented tangentially or circumferentially, so that the arms may flex toward one another in response to a longitudinal compressive force). However, the spring bridge may be any suitable shape that generally tends to shorten in the longitudinal direction in response a longitudinal compressive force (e.g., a "V"-shape, a "W"-shape, etc.).

As shown in FIG. 19, the spring bridges 1912 may be 90 degrees rotated relative to the position of two oppositely located sets of hinge extensions and hinge recesses. These bridges can be designed such that they withstand the required assembly force without significant deformation in the force direction, or that they deform to a predetermined ring distance. However, in some embodiments the bridges may be configured to break or fracture in response to a longitudinal compressive force when the hinge extension(s) and hinge recess(es) are coupled together. Additionally or alternatively, the bridges may be removed with the use of break islands or fracture elements, as described in further detail in PCT International Application Publication No. WO2016089202, which is incorporated herein by reference in its entirety. By applying forced bending of the instrument, such break islands will break such that the spring bridges are detached from the opposing hinge portions and can be removed. Furthermore, after assembling the hinge (and optionally breaking spring bridge(s) 1912 and/or breaking any break islands), the assembled tube may become more flexible in its articulable region(s).

Figure 20:
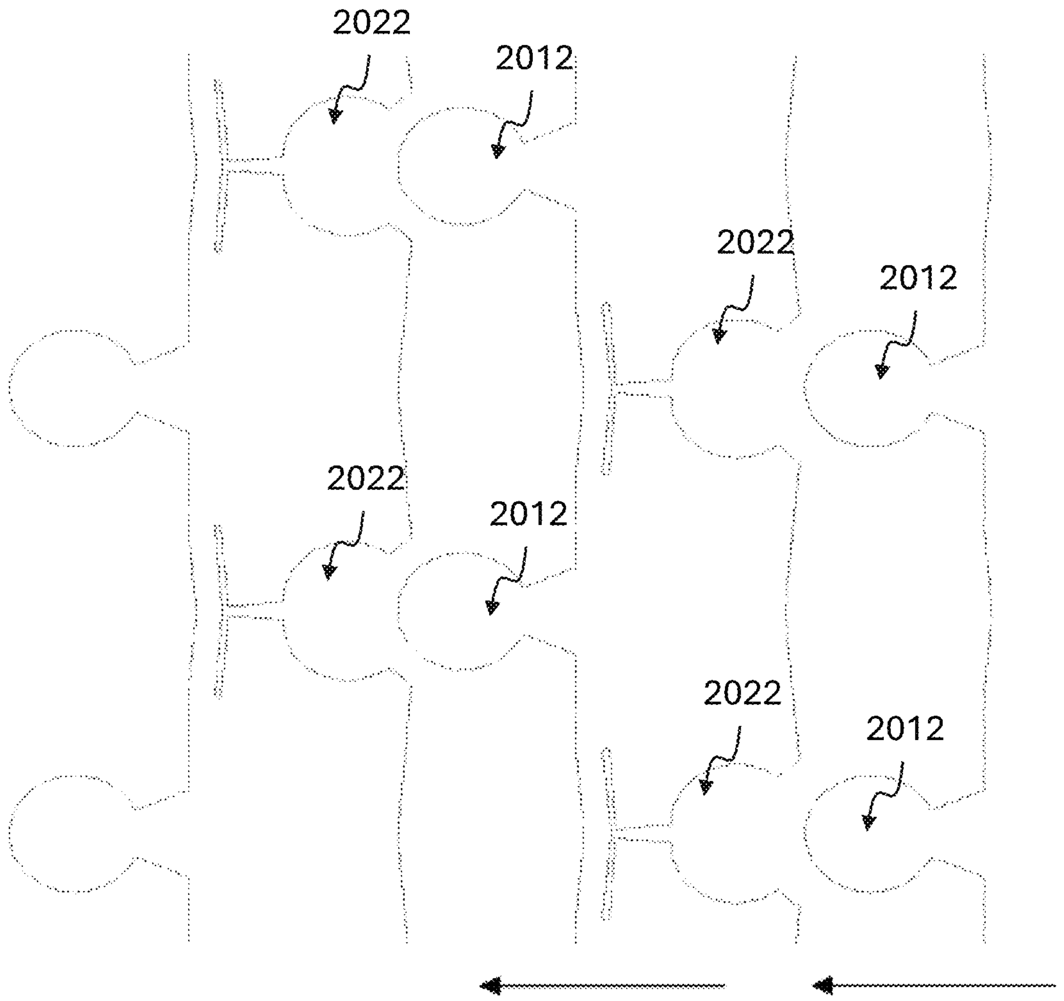

In some embodiments, the hinge portions may be formed such that before assembly of the hinge structures, the hinge recesses are already open, and the hinge recesses may be closed by a longitudinal assembly force. For example, as shown in FIG. 20, the hinge recesses 2022 may already be open as manufactured and in a rest condition, and sliding the hinge extensions 2012 into the hinge recesses 2022 may require minimal or no force. To close the hinge recesses 2022, a higher longitudinal force may be applied to close the recesses to the shape as shown in FIG. 18. In this case no assembly bridges like the spring bridges 1912 as in FIG. 19 are needed, and assembly can be performed without the assembling each hinge portion individually. After assembly, it is possible to pull the hinge portions apart again or to deform the hinge portions such that the hinge recesses open up again. For example, such action may be performed when longitudinal pulling forces become too high during instrument use or when tangential forces become too high during torqueing use of the instrument.

Another phenomenon is that when the instrument body is compressed, the hinge portion recesses are forced in a closing direction and dependent on the magnitude of the compression force the friction force in the hinge increases. In some embodiments, the instrument body may be configured such that its shape is frozen or locked when a compression force to the body is applied when, for example, an instrument tool tip is actuated. Again, in applications where only direct transfer of movement at low mechanical loads is required, solutions as in FIGS. 17 through 20 can be made to work. In some configurations it may be difficult to make sure that after closing, elastic spring back of deformed material does not increase the play in the hinge to unacceptable levels. To overcome these issues, the hinge may include a ratchet mechanism that prevents opening of the recess once it is closed once.

Figure 21:
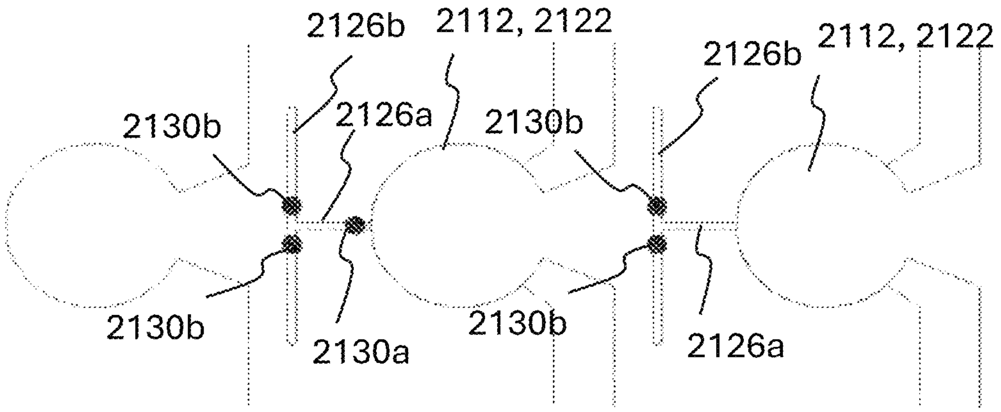

In some embodiments, one or more connections (e.g., spot welds, such as with laser welding) may be formed in the slot structure or other cut pattern, once the hinges are assembled via compressive force, to help strengthen the resulting hinge structure (e.g., help reduce the likelihood of the hinge extension decoupling from the hinge recess). FIG. 21 illustrates examples of such a weld pattern applied to hinge structures including hinge extensions 2112 and hinge recesses 2122 (shown as engaged in FIG. 21). As shown in FIG. 21, weld spots **2130*b* on the second slots 2126*b* would help prevent opening of these slots 2126*b* and therefore would help prevent the opening of the recess 2122. In some embodiments, the weld spots 2130*b* may be applied while the tubular member is loaded in longitudinal compression and hinge projections 2112 are received in the hinge recesses 2122, which may help lock the hinge structure in a configuration in which the hinge structure exhibits zero (or sufficiently low) play. Additionally or alternatively, other weld spots may be applied to the slot pattern, such as weld spot(s) 2130*a* on the first slot 2126*a*. The weld spots 2130*a*, 2130*b*, etc. may withstand compression and/or tension so as to prevent the hinge recesses 2122 from opening (e.g., hold the hinge recesses 2122** in a closed state) as well as strengthen the integral hinge portion strength and stiffness. Furthermore, the spot size, location, and/or the applied laser power may be selected such that a predetermined area of material is molten during the welding. At solidifying and cooling, this amount of material shrinks. This shrinking of the base material can be used to further enhance the elimination of play in the hinge and even can be used to preset a certain amount of mechanical force or friction pre-tension on the hinge. For example, the individual weld spot location(s), individual weld spot size, and/or the relative weld spot locations or pattern of multiple weld spots may be selected or otherwise tuned to achieve a desired amount of pre-tension in the hinge (e.g., amount of "shrink" or "squeeze" within the hinge).

Another method of locking the hinge recess in a closed state is to apply an inner or outer ring, or part of a ring, over the ring-shaped hinge portion, and weld it in place. In this way, also the integral ring strength and stiffness is assured.

Figure 22A:
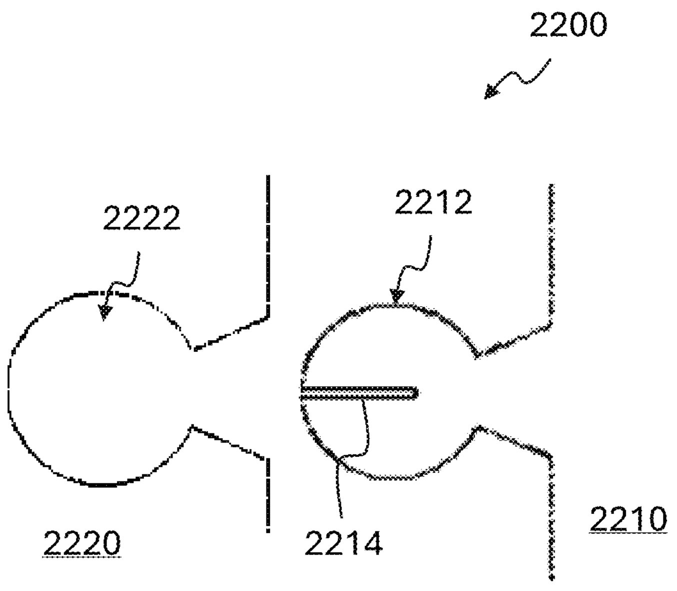

As another example of feature(s) to improve the ability of the hinge recess to receive the hinge extension, FIG. 22A illustrates an example hinge 2200 with a hinge extension including a slot pattern. Hinge 2200 includes two adjacent hinge portions 2210 and 2220 (similar to first hinge portion 1410 and second hinge portion 1420, respectively), where a first hinge portion 2210 includes a hinge extension 2212 such as a protruding circular projection, and a second hinge portion 2220 includes a hinge recess 2222. The first hinge portion 2210 may include a slot pattern including at least a first slot 2214 extending from a distal or free end of the hinge extension 2212 toward a center of the hinge extension. The slot 2214 may, for example, allow the hinge extension 2212 to be compressed (e.g., compressed tangentially) and have a reduced diameter, so as to be received within the hinge recess 2222 more easily. Although the slot 2214 is shown in FIG. 22A as being generally linear, it should be understood that in other embodiments, the slot 2214 may be other suitable shapes configured to improve the ability of the hinge extension to compress (e.g., compress tangentially). For example, the slot 2214 may be V-shaped, having a wider width at the free end of the hinge extension 2212 and narrower width as the slot extends toward the center of the hinge extension 2212. As another example, the slot 2214 may be curved or sinusoidal. In some embodiments, a tubular member (e.g., intermediate member) may include a series of hinge portions that include adjacent pairs of hinges 2200 (and/or other hinges having hinge extensions with a slot). Additionally or alternatively, in some embodiments, a tubular member may include one or more spring bridges connecting adjacent hinge portions forming multiple hinges 2200 (or other hinges having hinge extensions with a slot), which may also help (at least temporarily) hold the hinge portions in approximate desired positions relative to each other until full assembly with compressive force, similar to that described above with respect to FIG. 19.

Figure 22B:
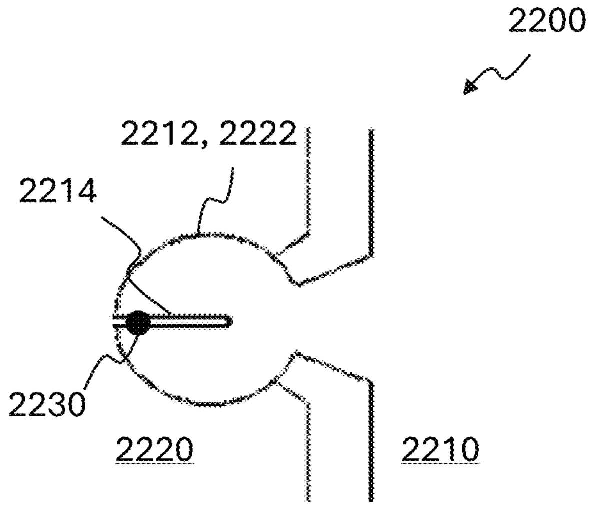

Similar to that described above with respect to FIG. 21, in some embodiments, one or more connections (e.g., spot welds, such as with laser welding) may be formed in the slot of a hinge extension, once the hinges are assembled via compressive force. For example, as shown in FIG. 22B, one or more weld spots 2230 may be applied to the slot 2214, after the hinge extension 2212 is received within the hinge recess 2222, which may help lock the hinge structure in a configuration in which the hinge structure exhibits zero (or sufficiently low) play. For example, the one or more weld spots 2230 may be configured to help maintain a certain width of the slot 2214 (e.g., with the hinge extension in a non-compressed, or expanded state) such that the hinge extension and the hinge recess are coupled together with zero or sufficiently low play. Although a single weld spot 2230 is shown in FIG. 22B, it should be understood that in some embodiments, multiple weld spots 2230 may be applied to a slot pattern on the hinge extension. Furthermore, similar to that described above with respect to FIG. 21, the individual weld spot location(s), individual weld spot size, the relative weld spot locations or pattern of multiple weld spots, and/or applied laser power for each weld spot may be selected or otherwise tuned to achieve a desired amount of pre-tension in the hinge (e.g., amount of "shrink" or "squeeze" within the hinge).

In some embodiments, a hinge may include both a hinge recess with a slot pattern configured to enable the hinge recess to open and expand in diameter (e.g., similar to that shown in FIG. 17) and a hinge extension with a slot pattern configured to enable the hinge extension to compress and reduce in diameter (e.g., similar to that shown in FIG. 22A).

It will be clear to a person skilled in the art that the scope of the invention is not limited to the examples discussed in the foregoing, but that several amendments and modifications thereof are possible without deviating from the scope of the invention as defined in the attached claims. While the invention has been illustrated and described in detail in the figures and the description, such illustration and description are to be considered illustrative or exemplary only, and not restrictive. The present invention is not limited to the disclosed embodiments but comprises any combination of the disclosed embodiments that can come to an advantage.

Variations to the disclosed embodiments can be understood and effected by a person skilled in the art in practicing the claimed invention, from a study of the figures, the description and the attached claims. In the description and claims, the word "comprising" does not exclude other elements, and the indefinite article "a" or "an" does not exclude a plurality. In fact it is to be construed as meaning "at least one". The mere fact that certain features are recited in mutually different dependent claims does not indicate that a combination of these features cannot be used to advantage. Any reference signs in the claims should not be construed as limiting the scope of the invention. Features of the above described embodiments and aspects can be combined unless their combining results in evident technical conflicts.

The present technology relates to a method of forming a hinge in a tube structure comprising the actions of manufacturing a first hinge portion and a second hinge portion such that

- the first hinge portion has a first structure at a first location and a second structure at a second location 180 degrees rotated relative to the first location as seen in a tangential direction of the tube structure;
- the second hinge portion has a third structure at a third location and a fourth structure at a fourth location 180 degrees rotated relative to the third location as seen in a tangential direction of the tube structure;
- such that the first structure and the third structure may be connected to one another by a first snap-fit connection, the second structure and the fourth structure may be connected to one another by a second snap-fit connection and after the first snap-fit connection and second snap-fit connection have been made the first and second hinge portions can rotate relative to one another about a line connecting the first location and the second location.

In some embodiments, a method of making a steerable tube may include forming a first hinge portion in a wall of an elongated tubular member, wherein the first hinge portion comprises a hinge extension having a first arcuate articulating edge, forming a second hinge portion in the wall of the tubular member, wherein the second hinge portion comprises a hinge recess having a second arcuate articulating edge complementary to the first arcuate articulating edge, and compressing the tubular member along a longitudinal axis of the tubular member such that the hinge recess receives the hinge extension and the first and second arcuate articulating edges engage to couple the first and second hinge portions together in a snap-fit connection.

The method may comprise manufacturing the first and second hinge portions such that

- the first structure includes a first circular protrusion and the second structure includes a first cutting pattern with a first circular recess or vice versa; and
- the third structure includes a second circular protrusion and the fourth structure includes a second cutting pattern with a second circular recess or vice versa.

The first cutting pattern may include a first slot pattern arranged to assist in opening of the first circular recess when the first circular protrusion is moved into the first circular recess, and the second cutting pattern may include a second slot pattern arranged to assist in opening of the second circular recess when the second circular protrusion is moved into the second circular recess.

The method may comprise the action of moving the first and second hinge portions towards one another after the manufacturing action such as to make the first and second snap-fit connections.

The method of forming a hinge may be such that, after the moving action, the first and second snap-fit connections show zero play.

The first and third structures in the first snap-fit connection may be clamping one another and the second and fourth structures in the second snap-fit connection may be clamping one another, such that a rotation force is required to rotate the first and second hinge portions relative to one another.

The manufacturing action may include manufacturing the first and second hinge portions from a single tube.

The present technology also relates to a method of making an invasive instrument including a tube structure with a hinge made by the method as defined herein above.

EXAMPLES

The subject technology is illustrated, for example, according to various aspects described below, including with reference to FIGS. 1-22B. Various examples of aspects of the subject technology are described as numbered clauses (1, 2, 3, etc.) for convenience. These are provided as examples and do not limit the subject technology.

1. A method of making an articulable tube, the method comprising:
   - forming a first hinge portion in a wall of an elongated tubular member, wherein the first hinge portion comprises a hinge extension having a first arcuate articulating edge;
   - forming a second hinge portion in the wall of the tubular member, wherein the second hinge portion comprises a hinge recess having a second arcuate articulating edge complementary to the first arcuate articulating edge, and
   - compressing the tubular member along a longitudinal axis of the tubular member such that the hinge recess receives the hinge extension and the first and second arcuate articulating edges engage to couple the first and second hinge portions together in a snap-fit connection.

2. The method of clause 1, wherein the first and second articulating edges are profiled toward a centerline of the tubular member.

3. The method of clause 1 or 2, wherein at least one of the hinge extension or the hinge recess is at least partially circular.

4. The method of any one of clauses 1-3, wherein forming the second hinge portion comprises forming a slot pattern configured to enable the hinge recess to widen when receiving the hinge extension.

5. The method of any one of clauses 1-4, wherein forming the first hinge portion and forming the second hinge portion are performed by laser cutting with a laser beam having a beam width, and wherein the coupled first and second hinge portions are separated by a gap narrower than the beam width.

6. The method of any one of clauses 1-5, wherein the snap-fit connection between the first and second hinge portions exhibits substantially zero play.

7. The method of any one of clauses 1-6, further comprising forming a flexible bridge member in the tubular member, the bridge member connecting the first hinge portion and the second hinge portion.

8. The method of clause 7, wherein compressing the tubular member comprises longitudinally compressing the bridge member to allow the first and second hinge portions to couple together.

9. The method of clause 8, wherein longitudinally compressing the bridge member comprises fracturing the bridge member.

10. The method of any one of clauses 1-9, wherein:

forming the first hinge portion further comprises forming a second hinge extension positioned 180 degrees circumferentially offset from the first hinge extension, and forming the second hinge portion further comprises forming a second hinge recess positioned 180 degrees circumferentially offset from the first hinge recess.

11. An articulable tube, comprising:

an elongated tubular member comprising:

a first hinge portion formed in a wall of the tubular member, wherein the first hinge portion comprises a hinge extension having a first arcuate articulating edge;

a second hinge portion formed in the wall of the tubular member, wherein the second hinge portion comprises a hinge recess having a second arcuate articulating edge;

wherein the hinge extension is received in the hinge recess such that the first and second arcuate articulating edges are engaged to thereby couple the first and second hinge portions together in a snap-fit connection.

12. The articulable tube of clause 11, wherein the first and second articulating edges are profiled toward a centerline of the tubular member.

13. The articulable tube of clause 11 or 12, wherein at least one of the hinge extension or the hinge recess is at least partially circular.

14. The articulable tube of any one of clauses 11-13, wherein the second hinge portion comprises a slot pattern configured to enable the hinge recess to widen when receiving the hinge extension.

15. The articulable tube of any one of clauses 11-14, wherein the snap-fit connection between the first and second hinge portions exhibits substantially zero play.

16. The articulable tube of any one of clauses 11-15, further comprising a flexible bridge member connecting the first hinge portion and the second hinge portion.

17. The articulable tube of any one of clauses 11-16, wherein the hinge extension is a first hinge extension and the hinge recess is a first hinge recess, wherein the first hinge portion further comprises a second hinge extension positioned 180 degrees circumferentially offset from the first hinge extension, and wherein the second hinge portion further comprises a second hinge recess positioned 180 degrees circumferentially offset from the first hinge recess.

18. The articulable tube of any one of clauses 11-17, wherein the first hinge portion and the second hinge portion are formed by laser cutting the tubular member.

19. An articulable tube assembly comprising a plurality of tubes including the articulable tube of any one of clauses 11-18 and a second tube arranged coaxially within or around the articulable tube.

20. A method of making an articulable tube assembly, the method comprising:

forming, with a first cut, a hinge extension in a wall of an elongated tubular member having a longitudinal axis, wherein the hinge extension has a first articulating surface located at a first axial location along the longitudinal axis;

forming, with a second cut, a hinge recess in the wall of the tubular member, wherein the hinge recess has a second articulating surface located at a second axial location along the longitudinal axis, wherein the second axial location is longitudinally offset from the first axial location;

urging the hinge extension and the hinge recess toward each other such that first and second articulating surfaces engage to couple the hinge extension and the hinge recess together in a snap-fit connection, thereby forming an articulable tube with at least one hinge;

placing the articulable tube coaxially within or around a second tubular member; and coupling the articulable tube and the second tubular member together.

CONCLUSION

Although many of the embodiments are described above with respect to steerable medical devices and methods for making such steerable medical devices, the technology is applicable to other applications and/or other approaches. Moreover, other embodiments in addition to those described herein are within the scope of the technology. Additionally, several other embodiments of the technology can have different configurations, components, or procedures than those described herein. A person of ordinary skill in the art, therefore, will accordingly understand that the technology can have other embodiments with additional elements, or the technology can have other embodiments without several of the features shown and described above with reference to FIGS. 1-22B.

The descriptions of embodiments of the technology are not intended to be exhaustive or to limit the technology to the precise form disclosed above. Where the context permits, singular or plural terms may also include the plural or singular term, respectively. Although specific embodiments of, and examples for, the technology are described above for illustrative purposes, various equivalent modifications are possible within the scope of the technology, as those skilled in the relevant art will recognize. For example, while steps are presented in a given order, alternative embodiments may perform steps in a different order. The various embodiments described herein may also be combined to provide further embodiments.

As used herein, the terms “generally,” “substantially,” “about,” and similar terms are used as terms of approximation and not as terms of degree, and are intended to account for the inherent variations in measured or calculated values that would be recognized by those of ordinary skill in the art.

Moreover, unless the word “or” is expressly limited to mean only a single item exclusive from the other items in reference to a list of two or more items, then the use of “or” in such a list is to be interpreted as including (a) any single item in the list, (b) all of the items in the list, or (c) any combination of the items in the list. Additionally, the term "comprising" is used throughout to mean including at least the recited feature(s) such that any greater number of the same feature and/or additional types of other features are not precluded. It will also be appreciated that specific embodiments have been described herein for purposes of illustration, but that various modifications may be made without deviating from the technology. Further, while advantages associated with certain embodiments of the technology have been described in the context of those embodiments, other embodiments may also exhibit such advantages, and not all embodiments need necessarily exhibit such advantages to fall within the scope of the technology. Accordingly, the disclosure and associated technology can encompass other embodiments not expressly shown or described herein.

I claim:

1. A method of making an articulable tube, the method comprising:

forming a first hinge portion in a wall of an elongated tubular member, wherein the first hinge portion comprises a hinge extension having a first arcuate articulating edge;

forming a second hinge portion in the wall of the tubular member, wherein the second hinge portion comprises a hinge recess having a second arcuate articulating edge complementary to the first arcuate articulating edge, and compressing the tubular member along a longitudinal axis of the tubular member such that the hinge recess receives the hinge extension and the first and second arcuate articulating edges engage to couple the first and second hinge portions together in a snap-fit connection, wherein the second hinge portion comprises a slot pattern configured to enable the hinge recess to widen when the hinge recess receives the hinge extension.

2. The method of claim 1, wherein the first and second articulating edges are profiled toward a centerline of the tubular member.

3. The method of claim 1, wherein at least one of the hinge extension or the hinge recess is at least partially circular.

4. The method of claim 1, wherein forming the first hinge portion and forming the second hinge portion are performed by laser cutting with a laser beam having a beam width, and wherein the coupled first and second hinge portions are separated by a gap narrower than the beam width.

5. The method of claim 1, wherein the snap-fit connection between the first and second hinge portions exhibits substantially zero play.

6. The method of claim 1, further comprising forming a flexible bridge member in the tubular member, the bridge member connecting the first hinge portion and the second hinge portion.

7. The method of claim 6, wherein compressing the tubular member comprises longitudinally compressing the bridge member to allow the first and second hinge portions to couple together.

8. The method of claim 7, wherein longitudinally compressing the bridge member comprises fracturing the bridge member.

9. The method of claim 1, wherein the hinge extension is a first hinge extension and the hinge recess is a first hinge recess:

forming the first hinge portion further comprises forming a second hinge extension positioned 180 degrees circumferentially offset from the first hinge extension, and forming the second hinge portion further comprises forming a second hinge recess positioned 180 degrees circumferentially offset from the first hinge recess.

10. The method of claim 1, further comprising welding at least a portion of the slot pattern into a fixed state after the first and second hinge portions are coupled together.

11. An articulable tube, comprising:

an elongated tubular member comprising:

a first hinge portion formed in a wall of the tubular member, wherein the first hinge portion comprises a hinge extension having a first arcuate articulating edge;

a second hinge portion formed in the wall of the tubular member, wherein the second hinge portion comprises a hinge recess having a second arcuate articulating edge;

wherein the hinge extension is received in the hinge recess such that the first and second arcuate articulating edges are engaged to thereby couple the first and second hinge portions together in a snap-fit connection, wherein the second hinge portion comprises a slot pattern configured to enable the hinge recess to widen when the hinge recess receives the hinge extension.

12. The articulable tube of claim 11, wherein the first and second articulating edges are profiled toward a centerline of the tubular member.

13. The articulable tube of claim 11, wherein at least one of the hinge extension or the hinge recess is at least partially circular.

14. The articulable tube of claim 11, wherein the snap-fit connection between the first and second hinge portions exhibits substantially zero play.

15. The articulable tube of claim 11, further comprising a flexible bridge member connecting the first hinge portion and the second hinge portion.

16. The articulable tube of claim 11, wherein the hinge extension is a first hinge extension and the hinge recess is a first hinge recess, wherein the first hinge portion further comprises a second hinge extension positioned 180 degrees circumferentially offset from the first hinge extension, and wherein the second hinge portion further comprises a second hinge recess positioned 180 degrees circumferentially offset from the first hinge recess.

17. The articulable tube of claim 11, wherein the first hinge portion and the second hinge portion are formed by laser cutting the tubular member.

18. An articulable tube assembly comprising a plurality of tubes including the articulable tube of claim 11 and a second tube arranged coaxially within or around the articulable tube.

19. The articulable tube of claim 11, further comprising one or more weld spots applied to the slot pattern.

20. A method of making an articulable tube assembly, the method comprising:

forming, with a first cut, a hinge extension in a wall of an elongated tubular member having a longitudinal axis, wherein the hinge extension has a first articulating surface located at a first axial location along the longitudinal axis;

forming, with a second cut, a hinge recess in the wall of the tubular member, wherein the hinge recess has a second articulating surface located at a second axial location along the longitudinal axis, wherein the second axial location is longitudinally offset from the first axial location;

urging the hinge extension and the hinge recess toward each other such that the first and second articulating surfaces engage to couple the hinge extension and the hinge recess together in a snap-fit connection, thereby forming an articulable tube with at least one hinge;

placing the articulable tube coaxially within or around a second tubular member; and coupling the articulable tube and the second tubular member together, wherein the first hinge portion comprises a slot pattern configured to enable the hinge extension to compress when the hinge recess receives the hinge extension.

* * * * *